(12) United States Patent
Gerlach et al.

(10) Patent No.: US 11,549,889 B2
(45) Date of Patent: Jan. 10, 2023

(54) METHOD FOR DETECTING A BINDING OF ANTIBODIES FROM A PATIENT SAMPLE TO DOUBLE-STRANDED DNA USING CRITHIDIA LUCILIAE CELLS AND FLUORESCENCE MICROSCOPY

(71) Applicant: EUROIMMUN Medizinische Labordiagnostika AG, Lübeck (DE)

(72) Inventors: Stefan Gerlach, Groß Groenau (DE); Christian Marzahl, Erlangen (DE); Maick Danckwardt, Rondeshagen (DE); Joern Voigt, Luebeck (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 473 days.

(21) Appl. No.: 16/821,056

(22) Filed: Mar. 17, 2020

(65) Prior Publication Data
US 2020/0300764 A1 Sep. 24, 2020

(30) Foreign Application Priority Data

Mar. 18, 2019 (EP) .................... 19163553

(51) Int. Cl.
*G06K 9/00* (2022.01)
*G01N 21/64* (2006.01)
(Continued)

(52) U.S. Cl.
CPC ....... *G01N 21/6458* (2013.01); *G01N 33/564* (2013.01); *G01N 33/582* (2013.01);
(Continued)

(58) Field of Classification Search
CPC ............. B01F 31/23; B01L 2300/0636; B01L 2300/0809; B01L 2300/0829; B01L 2300/0887; B01L 2300/089; B01L 2400/0406; B01L 2400/0457; B01L 3/502746; B01L 3/5085; B01L 3/5088; G01N 1/2813; G01N 1/312; G01N 21/6458; G01N 2800/104; G01N 33/564; G01N 33/582; G01N 21/6486; G01N 2333/495; G01N 2333/522; G01N 2333/523; G01N 2333/525; G01N 2333/5428;
(Continued)

(56) References Cited

U.S. PATENT DOCUMENTS

2018/0286040 A1* 10/2018 Sashida ................ G06V 10/454
2018/0364229 A1* 12/2018 James .................... G16B 5/00
2019/0371425 A1* 12/2019 Kuo ..................... G06T 7/0012

FOREIGN PATENT DOCUMENTS

EP 3 591 403 1/2020

OTHER PUBLICATIONS

Xu et al, "A Deep Convolutional Neural Network for Segmenting and Classifying epithelial and Stromal Regions in histopathological images", Neuralcomputing 191 (2016) 214-223.*
(Continued)

*Primary Examiner* — Tom Y Lu
(74) *Attorney, Agent, or Firm* — Grüneberg and Myers, PLLC

(57) ABSTRACT

A method and a device are useful for detecting a binding of autoantibodies from a patient sample to double-stranded deoxyribonucleic acid (DNA) using *Crithidia luciliae* cells by fluorescence microscopy and by digital image processing.

15 Claims, 24 Drawing Sheets

(51) Int. Cl.
*G01N 33/58* (2006.01)
*G02B 21/00* (2006.01)
*G01N 33/564* (2006.01)
*G06T 7/00* (2017.01)

(52) U.S. Cl.
CPC ........ *G02B 21/0076* (2013.01); *G06T 7/0012* (2013.01); *G06T 7/0014* (2013.01); *G02B 21/008* (2013.01); *G06T 2207/20084* (2013.01)

(58) Field of Classification Search
CPC ... G01N 2333/5434; G01N 2333/5443; G01N 2333/545; G01N 2333/555; G01N 2333/575; G01N 33/6863; G02B 21/0076; G02B 21/008; G02B 21/34; G06T 2207/10024; G06T 2207/10056; G06T 2207/10064; G06T 2207/20081; G06T 2207/20084; G06T 2207/30024; G06T 7/0012; G06T 2207/20021; G06T 7/0014; G06T 7/90; G06N 3/0454; G06N 3/08; G06V 20/69; G16B 40/00; G16B 5/00; G16B 5/20; G16H 30/40; G16H 50/20
See application file for complete search history.

(56) References Cited

OTHER PUBLICATIONS

Gerlach et al., "*Evaluation of Crithidia luciliae IFT can be reliably automated with EUROPATTERN*", 31st Annual Meeting of the Association of Medical Laboratory Immunologists (AMLI), Scottsdale, USA, Aug. 2018, 1 page.
Extended Search Report dated Jun. 14, 2019 in European Application No. 191663553.1 with English translation, 14 pages.
Bayramoglu et al., 2015 IEEE 15th International Conference on Bioinformatics and Bioengineering (BIBE); 2015, pp. 1-6.
Gerlach et al., Clinical Chemistry; 2018, 64(1):S125.
Gerlach et al., Journal of Immunology Research; Jan. 2015, pp. 1-8.
Lakos, et al., Journal of Immunological Methods; 2016, 433(1):17-22.
Soda et al., Artificial Intelligence in Medicine; 2011, 51:67-74.

\* cited by examiner

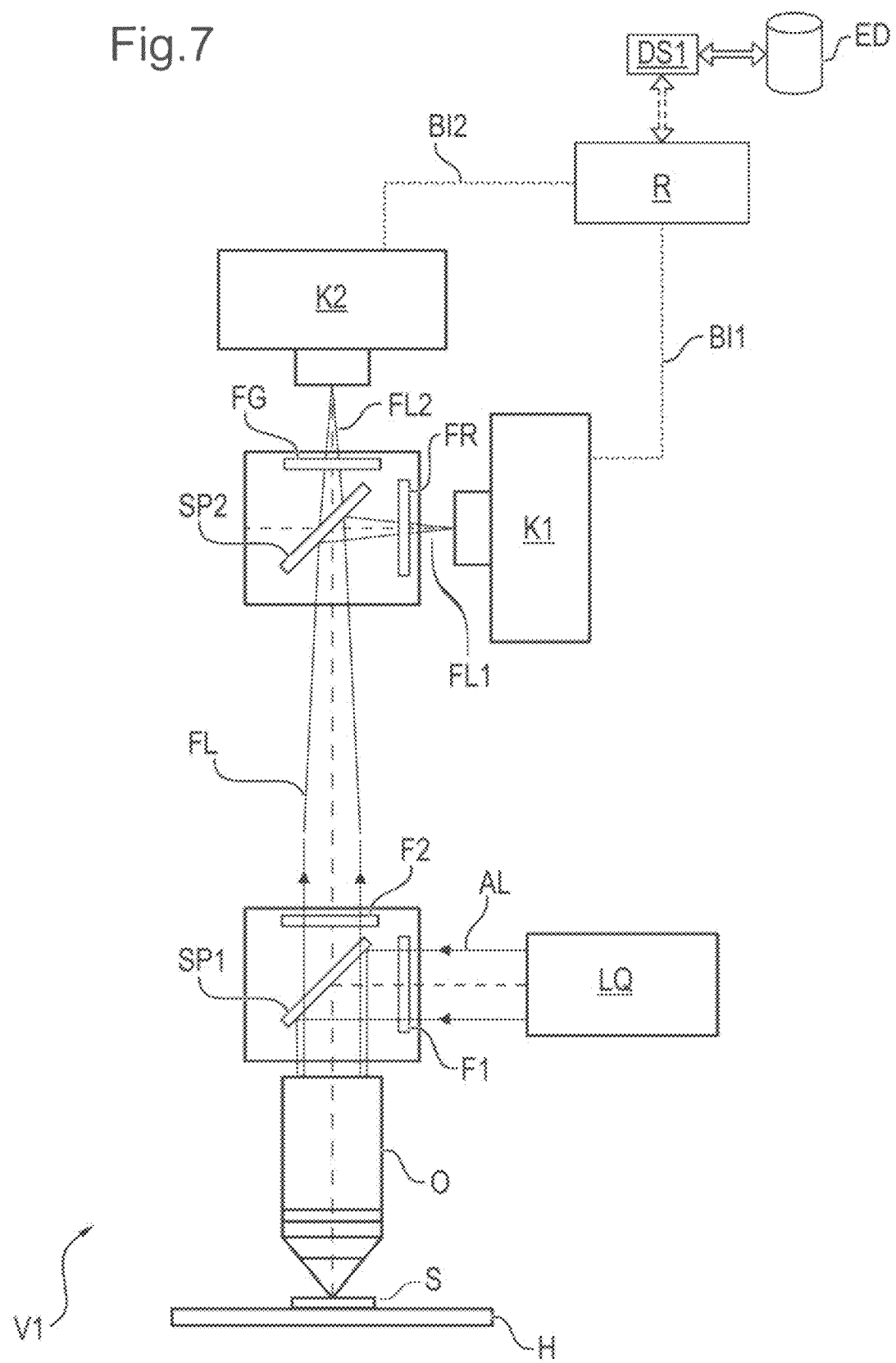

Fig.8 KSR
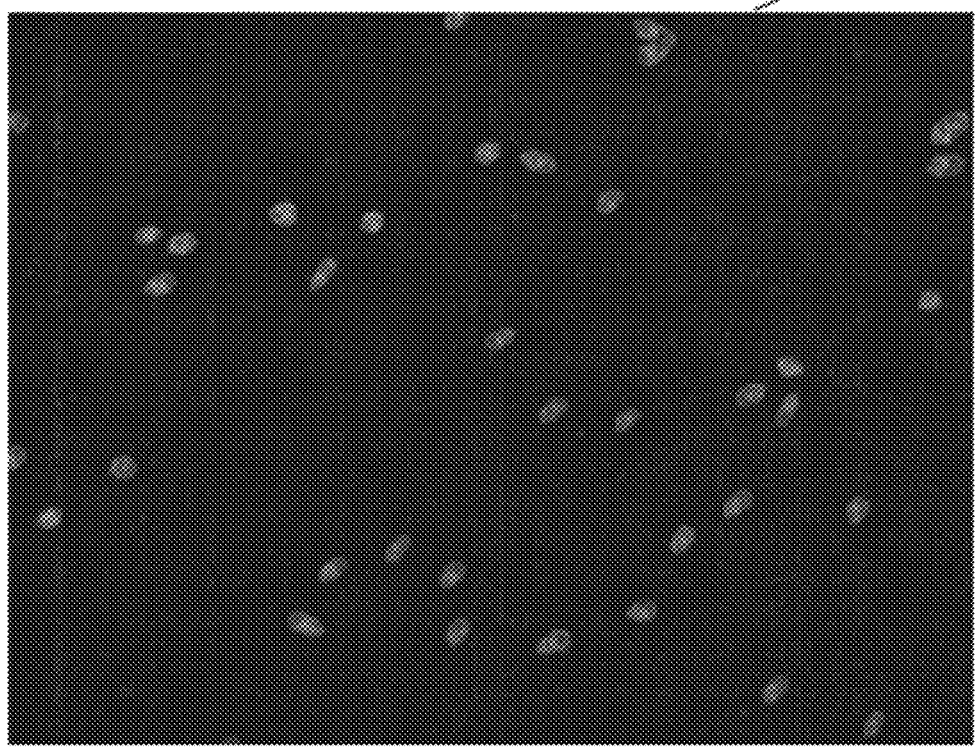
Fig.9 BSR
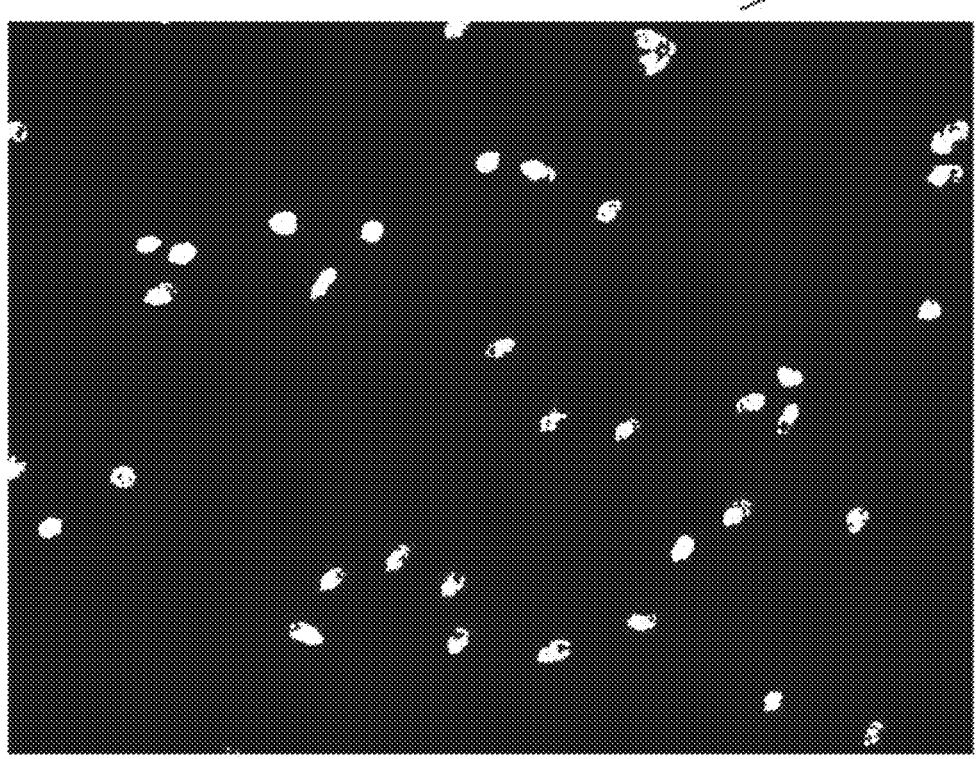

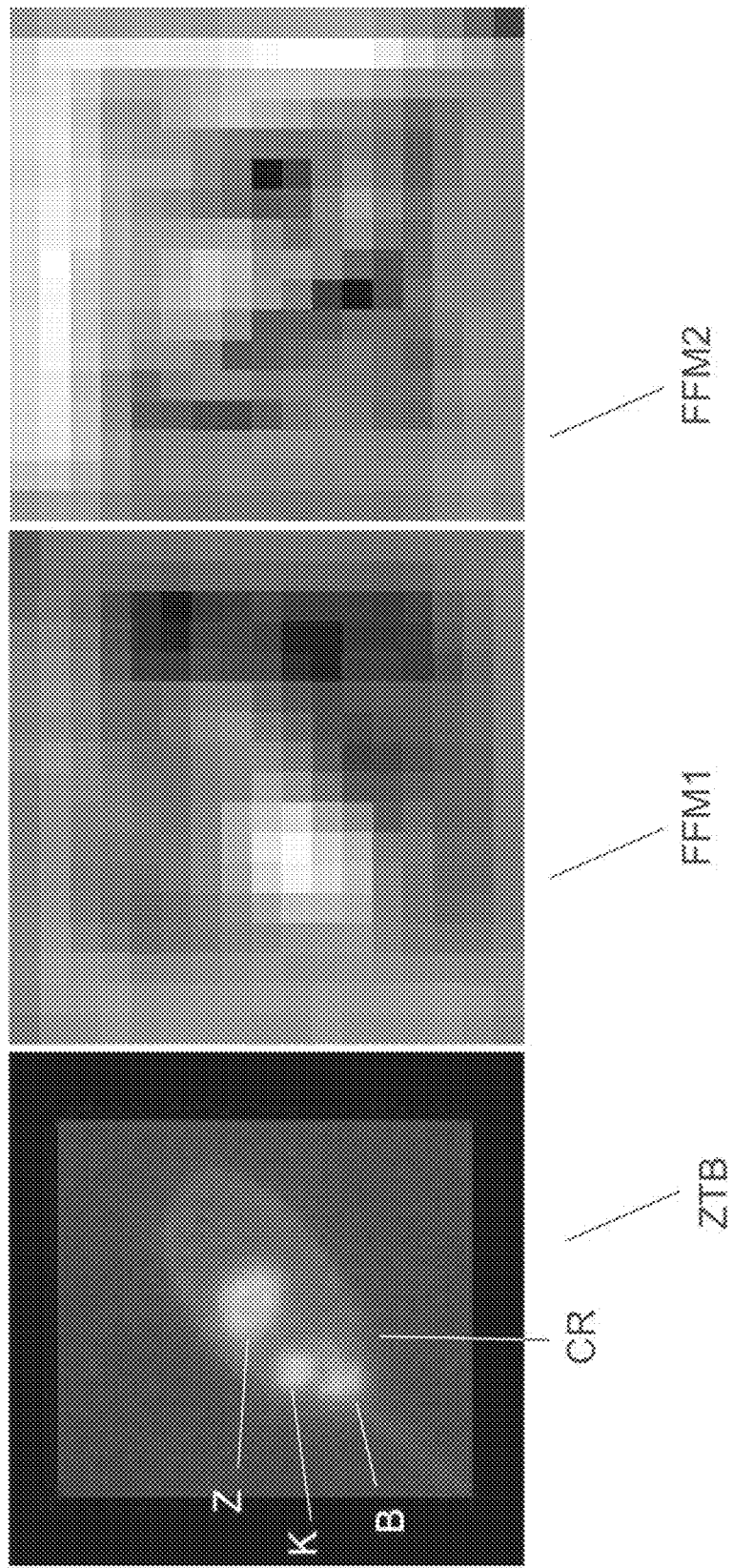

METHOD FOR DETECTING A BINDING OF ANTIBODIES FROM A PATIENT SAMPLE TO DOUBLE-STRANDED DNA USING CRITHIDIA LUCILIAE CELLS AND FLUORESCENCE MICROSCOPY

CROSS-REFERENCE TO RELATED APPLICATION

The present application claims the benefit to European application EP 19163553.1, filed on Mar. 18, 2019, which is incorporated by reference in its entirety.

BACKGROUND OF THE INVENTION

Field of the Invention

The invention relates to a method and a device for detecting a binding of autoantibodies from a patient sample to double-stranded deoxyribonucleic acid (DNA) using *Crithidia luciliae* cells by means of fluorescence microscopy and by means of digital image processing.

Discussion of the Background

The detection of autoantibodies against deoxyribonucleic acids (DNA) is, for example, of crucial importance for the diagnosis of SLE (systemic lupus erythematosus). Here, a fundamental distinction must be made between two types: antibodies against dsDNA and antibodies against single-stranded, denatured DNA (ssDNA). Antibodies against dsDNA react with epitopes within the deoxyribose phosphate scaffold of DNA. By contrast, antibodies against ssDNA predominantly bind themselves to epitopes from the region of the purine and pyrimidine bases. However, they can also recognize epitopes of the deoxyribose phosphate scaffold. Anti-dsDNA antibodies are found almost exclusively in SLE. Their prevalence is 20% to 90% depending on the detection method and disease activity. Anti-dsDNA antibodies are sometimes also detected in patients with other autoimmune diseases and infections and, in rare cases, in clinically healthy individuals. The latter develop, in 85% of cases, an SLE within 5 years after the first anti-dsDNA detection. However, it is not possible to completely rule out an SLE if no antibodies against dsDNA are present. SLE is a systemic autoimmune disease from the group of connective tissue diseases. Diagnosis is guided by the 1997 update of the 11 criteria from the American College of Rheumatology (ACR). If 4 of the 11 criteria are present, it is possible to make the diagnosis of an SLE with 80% to 90% certainty.

An indirect immunofluorescence is an in vitro test for the determination of human antibodies against dsDNA. For example, so-called BIOCHIPs coated with *Crithidia luciliae* smears can serve as substrates. These are, for example, incubated with diluted patient samples. In the event of positive reactions, specific antibodies bind themselves to the antigens. Bound antibodies (IgG) are, for example, stained with fluorescein-labelled anti-human antibodies in a second incubation step and visualized under a fluorescence microscope.

Providing a substrate in which multiple *Crithidia luciliae* cells are fixed on the substrate is therefore known from the related art. Such fixing can, for example, be effected by means of ethanol.

The substrate is then incubated with a patient sample, preferably diluted blood serum, the patient sample potentially having the autoantibodies to be detected. According to the related art, the cells or the substrate can then be incubated with a so-called conjugate which has secondary antibodies labelled with a, for example, green fluorescent dye.

After irradiation of the incubated substrate with excitation light, a fluorescence radiation emitted by the green fluorescent dye can then be acquired as a fluorescence microscopy micrograph.

By way of example, such a micrograph is depicted in FIG. 1 as the image SB.

An individual *Crithidia* cell CR from FIG. 1 is depicted again in FIG. 2 in more detail.

Such a sub-image TB of one *Crithidia luciliae* cell CR clearly shows a staining on the kinetoplast K, which is also referred to as a mitochondrion. There are further stainings on the nucleus Z and on the basal body B.

For a reliable detection of a binding of autoantibodies from the patient sample to double-stranded DNA, it is crucial to detect a staining of multiple kinetoplasts in the fluorescence image SB of the substrate. As shown by FIG. 2, a binding or a staining may also be present for a nucleus Z and for a basal body B, meaning that the kinetoplast K must be reliably determined with respect to its position in the image by means of image processing.

By means of an evaluation with regard to a respective staining of respective kinetoplasts of respective *Crithidia luciliae* cells in the fluorescence image SB, it is then possible to ascertain altogether an averaged overall binding of autoantibodies from the patient sample to double-stranded DNA.

SUMMARY OF THE INVENTION

It is thus an object to provide a method using digital image processing for determining a binding of autoantibodies from a patient sample to double-stranded DNA, wherein a staining of different kinetoplast regions of different *Crithidia luciliae* cells within a fluorescence image can be reliably determined. The invention includes following embodiments:

1. Method for detecting a binding of autoantibodies from a patient sample to double-stranded deoxyribonucleic acid using *Crithidia luciliae* cells by means of fluorescence microscopy and by means of digital image processing,
    comprising
        provision of a substrate (S) which has multiple *Crithidia luciliae* cells (CR),
        incubation of the substrate (S) with the patient sample which potentially has the autoantibodies.
        incubation of the substrate (S) with a first fluorescent dye,
        incubation of the substrate (S) with secondary antibodies which have each been labelled with a second fluorescent dye,
        acquisition of a first fluorescence image (SR) of the substrate (S) in a first colour channel which corresponds to the first fluorescent dye,
        acquisition of a second fluorescence image (SG) of the substrate (S) in a second colour channel which corresponds to the second fluorescent dye,
    characterized by
        identification of respective first sub-images (ETB) in the first fluorescence image (SR) that each represent a respective *Crithidia luciliae* cell (CR),
        determination of respective second sub-images (ZTB) of the second fluorescence image (SG) that correspond to the respective first sub-images (ETB) of the first fluorescence image (SR), respective processing of at least one subset of the respective second sub-images (ZTB) by means of a pretrained convolutional neural network (CNN) for determining respective binding measures (IBM1, IBM2) which indicate a respective extent of a binding of autoantibodies in a respective kinetoplast region (K) of a respective *Crithidia luciliae* cell (CR) of a respective second sub-image (ZTB), determination of an overall binding measure (GBM) with regard to the binding of autoantibodies from the patient sample to double-stranded deoxyribonucleic acid on the basis of the respective binding measures (IBM1, IBM2).

2. Method according to embodiment 1,
comprising, for a respective second sub-image (ZTB),
selection of a respective subordinate image (SUB) of the respective second sub-image (ZTB), the respective subordinate image (SUB) representing a respective kinetoplast region (K) of a respective *Crithidia luciliae* cell (CR),
determination of the respective binding measure (IBM1) on the basis of the respective subordinate image (SUB),
and comprising furthermore determination of the overall binding measure (GBM) on the basis of the respective binding measures (IBM1, IBM2).

3. Method according to embodiment 1,
comprising
determination of a respective final feature map (FFM1) for a respective second sub-image (ZTB) by means of the convolutional neural network (CNN),
determination of a respective confidence measure (PKN) with regard to a presence of a binding of autoantibodies in a respective kinetoplast region (K) for the respective second sub-image (ZTB),
selection of a subset of the second sub-images (ZTB) on the basis of the determined confidence measures (PKN),
respective processing of the respective feature maps of the respective selected second sub-images for determining the respective binding measures (IBM1, IBM2),
determination of the overall binding measure (GBM) on the basis of the respective binding measures (IBM1, IBM2) of the respective selected second sub-images.

4. Method according to embodiment 3,
comprising, for a respective second sub-image (ZTB) from the selected subset,
selection of a respective subordinate image (SUB) of the respective second sub-image (ZTB) on the basis of a respective final feature map (FFM1) corresponding to the respective second sub-image (ZTB), the respective subordinate image (SUB) representing a respective kinetoplast region (K) of a respective *Crithidia luciliae* cell (CR),
determination of the respective binding measure (IBM1) on the basis of the respective subordinate image (SUB),
and comprising furthermore
determination of the overall binding measure (GBM) on the basis of the respective binding measures (IBM1, IBM2).

5. Method according to embodiment 4,
comprising, for a respective second sub-image (ZTB) from the selected subset,
ascertainment of a respective masking operator (BM) on the basis of the respective final feature map (FFM1),
selection of the respective subordinate image (SUB) of the respective second sub-image (ZTB) by means of application of the respective masking operator (BM) to the respective second sub-image (ZTB),
determination of the respective binding measure (IBM1) on the basis of the respective subordinate image (SUB),
and comprising
determination of the overall binding measure (GBM) on the basis of the respective binding measures (IBM1, IBM2).

6. Method according to embodiment 3,
wherein, in the course of a processing of a second sub-image (ZTB), the convolutional neural network (CNN),
in a first processing level (P1), generates a first set of resultant feature maps (RFM1) on the basis of the second sub-image (ZTB) by means of at least one first convolutional layer (LA1) and by means of application of multiple two-dimensional convolution kernels,
in a second processing level (P2),
generates a second set of resultant feature maps (RFM2) on the basis of the first set of two-dimensional feature maps (RFM1) by means of at least one second convolutional layer (LA2) and by means of application of multiple three-dimensional convolution kernels,
and furthermore generates a third set of resultant feature maps (RFM3) on the basis of the second set of two-dimensional feature maps (RFM2) by means of at least one third convolutional layer (LA3) and by means of application of multiple three-dimensional convolution kernels,
wherein the second set (RFM2) has a smaller number of resultant feature maps than the first set (RFM1) and wherein the third set (RFM3) has a larger number of resultant feature maps than the second set (RFM2).

7. Method according to embodiment 6,
wherein, in the second processing level (P2), the second convolutional layer (LA2) and the third convolutional layer (LA3) are in a sequence as sub-steps of a sequential processing path (PF1),
wherein, in the second processing level (P2), there is in parallel to the sequential processing path (PF1) a further processing path (PF2) in which the convolutional neural network (CNN) generates a fourth set (RFM4) of resultant feature maps on the basis of the first set (RFM1) of two-dimensional feature maps by means of at least one fourth convolutional layer (LA4),
wherein the convolutional neural network (CNN) generates on the basis of the third (RFM3) and the fourth set (RFM4) of resultant feature maps the final feature map (FFM1) corresponding to the second sub-image (ZTB),
and wherein the number of successive convolution layers in the parallel processing path (PF2) is smaller than the number of successive convolution layers in the sequential processing path (PF1).

8. Method according to embodiment 1, comprising
    acquisition of a first preliminary fluorescence image (EVB1) in the first colour channel using a predefined acquisition parameter (GF),
    determination of a brightness value (HW) indicating a brightness of the first preliminary fluorescence image of the first colour channel (EVFB1),
    modification of the acquisition parameter depending on the determined brightness value (HW),
    acquisition of a second preliminary fluorescence image (ZVFB1) in the first colour channel using the modified acquisition parameter (GF2),
    use of the second preliminary fluorescence image of the first colour channel (ZVFB1) as the first fluorescence image (SR) of the first colour channel.

9. Method according to embodiment 8, comprising
    acquisition of a first preliminary fluorescence image (EVB1) in the first colour channel using a predefined acquisition parameter (GF),
    determination of a brightness value (HW) indicating a brightness of the first preliminary fluorescence image of the first colour channel (EVFB1),
    establishment by means of the brightness value (HW) as to whether a brightness of the first preliminary fluorescence image of the first colour channel (EVFB1) corresponds to an expected brightness,
    in the event of the brightness of the first preliminary fluorescence image (EVFB1) of the first colour channel corresponding to the expected brightness, use of the first preliminary fluorescence image of the first colour channel (EVFB1) as the first fluorescence image (SR) of the first colour channel,
    in the event of the brightness of the first preliminary fluorescence image of the first colour channel (EVFB1) not corresponding to the expected brightness,
        modification of the acquisition parameter depending on the determined brightness value (HW),
    acquisition of a second preliminary fluorescence image in the first colour channel (ZVFB1) using the modified acquisition parameter (GF2),
    use of the second preliminary fluorescence image of the first colour channel (ZFB1) as the first fluorescence image (SR) of the first colour channel.

10. Method according to embodiment 1, comprising
    acquisition of a first preliminary fluorescence image (EVFB2) in the second colour channel using a predefined acquisition parameter (EP1).
    establishment of whether a brightness of the first preliminary fluorescence image (EVFB2) of the second colour channel exceeds a maximum brightness, in the event of the first preliminary fluorescence image of the second colour channel (EVFB2) not exceeding the maximum brightness, use of the first preliminary fluorescence image (EVFB2) as the second fluorescence image (SG) of the second colour channel,
    in the event of the first preliminary fluorescence image of the second colour channel (EVFB2) exceeding the maximum brightness, acquisition of a second preliminary fluorescence image in the second colour channel (ZVFB2) and use of the second preliminary fluorescence image of the second colour channel (ZVFB2) as the second fluorescence image of the second colour channel (SG).

11. Device (V1) for detecting a binding of autoantibodies from a patient sample to double-stranded deoxyribonucleic acid using *Crithidia luciliae* cells by means of fluorescence microscopy and by means of digital image processing, comprising
    a mounting device (H) for a substrate (S) which has multiple *Crithidia luciliae* cells (CR) and which has been incubated with a patient sample having the autoantibodies, with a first fluorescent dye and, furthermore, with secondary antibodies which have each been labelled with a second fluorescent dye,
    at least one image acquisition unit (K1, K2) for acquiring a first fluorescence image (SR) of the substrate in a first colour channel and, furthermore, for acquiring a second fluorescence image (SG) of the substrate (S) in a second colour channel,
    and comprising furthermore at least one computing unit (R) which is designed
    to identify respective first sub-images (ETB) in the first fluorescence image (SR) that each represent at least one *Crithidia luciliae* cell (CR),
    to determine respective second sub-images (ZTB) of the second fluorescence image (SG) that correspond to the respective first sub-images (ETB) of the first fluorescence image (SR),
    to respectively process at least one subset of the respective second sub-images (ZTB) by means of a pre-trained convolutional neural network (CNN) for determining respective binding measures (IBM1, IBM2) which indicate a respective extent of a binding of autoantibodies in a respective kinetoplast region (K) of a respective *Crithidia luciliae* cell (CR) of a respective second sub-image (ZTB)
    and to determine an overall binding measure (GBM) of a binding of autoantibodies from the patient sample to double-stranded deoxyribonucleic acid on the basis of the respective binding measures (IBM1, IBM2).

12. Computing unit (R) which is designed, in the course of a digital image processing,
    to receive a first fluorescence image (SR) which represents a staining of a substrate, which in turn has multiple *Crithidia luciliae* cells (CR), by a first fluorescent dye and to receive a second fluorescence image (SG) which represents a staining of the substrate by a second fluorescent dye,
    to identify respective first sub-images (ETB) in the first fluorescence image (SR) that each represent at least one *Crithidia luciliae* cell (CR),
    to determine respective second sub-images (ZTB) of the second fluorescence image (SG) that correspond to the respective first sub-images (ETB) of the first fluorescence image (SR),
    to respectively process at least one subset of the respective second sub-images (ZTB) by means of a pre-trained convolutional neural network (CNN) for determining respective binding measures (IBM1, IBM2) which indicate a respective extent of a binding of autoantibodies in a respective kinetoplast region (K) of a respective *Crithidia luciliae* cell (CR) of a respective second sub-image (ZTB)

and to determine an overall binding measure (GBM) of a binding of autoantibodies from the patient sample to double-stranded deoxyribonucleic acid on the basis of the respective binding measures (IBM1, IBM2).

13. Data network device (DV) comprising
    at least one data interface (DS4) for receiving a first fluorescence image (BI1, SR) which represents a staining of a substrate, which in turn has multiple *Crithidia luciliae* cells, by a first fluorescent dye and, furthermore, of a second fluorescence image (BI2, SG) which represents a staining of the substrate by a second fluorescent dye,
    and furthermore at least one computing unit (R) which is designed, in the course of a digital image processing,
        to identify respective first sub-images (ETB) in the first fluorescence image (SR) that each have at least one *Crithidia luciliae* cell (CR),
        to determine respective second sub-images (ZTB) of the second fluorescence image (SG) that correspond to the respective first sub-images (ETB) of the first fluorescence image (SR),
        to respectively process at least one subset of the respective second sub-images (ZTB) by means of a pretrained convolutional neural network (CNN) for determining respective binding measures (IBM1, IBM2) which indicate a respective extent of a binding of autoantibodies in a respective kinetoplast region (K) of a respective *Crithidia luciliae* cell (CR) of a respective second sub-image (ZTB)
        and to determine an overall binding measure (GBM) of a binding of autoantibodies from the patient sample to double-stranded deoxyribonucleic acid on the basis of the respective binding measures (IBM1, IBM2).

14. Method for digital image processing, comprising
    receiving of a first fluorescence image (SR) which represents a staining of a substrate (S), which in turn has multiple *Crithidia luciliae* cells (CR), by a first fluorescent dye and, furthermore, of a second fluorescent image (SG) which represents a staining of the substrate (S) by a second fluorescent dye,
    identification of respective first sub-images (ETB) in the first fluorescence image (SR) that each represent a *Crithidia luciliae* cell (CR),
    determination of respective second sub-images (ZTB) of the second fluorescence image (SG) that correspond to the respective first sub-images (ETB) of the first fluorescence image (SR),
    respective processing of at least one subset of the respective second sub-images (ZTB) by means of a pretrained convolutional neural network (CNN) for determining respective binding measures (IBM1, IBM2) which indicate a respective extent of a binding of autoantibodies in a respective kinetoplast region (K) of a respective *Crithidia luciliae* cell (CR) of a respective second sub-image (ZTB),
    determination of an overall binding measure (GBM) of a binding of autoantibodies from the patient sample to double-stranded deoxyribonucleic acid on the basis of the respective binding measures (IBM1, IBM2).

15. Computer program product (CPP)
    comprising commands which, upon the execution of the program by a computer, prompt said computer to carry out the method for digital image processing according to embodiment 14.

16. Data carrier signal (SI2) which transmits the computer program product (CPP) according to embodiment 15.

BRIEF DESCRIPTION OF DRAWINGS

FIG. 7 shows an exemplary embodiment of the device according to the invention, FIG. 8 shows a modified version of the fluorescence image of the first colour channel with increase in contrast, FIG. 9 shows a binary-value image derived from the contrast-increased fluorescence image from FIG. 8, FIG. 10*a* shows an exemplary second sub-image, FIG. 10*b* shows a first final feature map, FIG. 10*c* shows a second final feature map to be preferably determined.

DETAILED DESCRIPTION OF THE INVENTION

Figure 1:
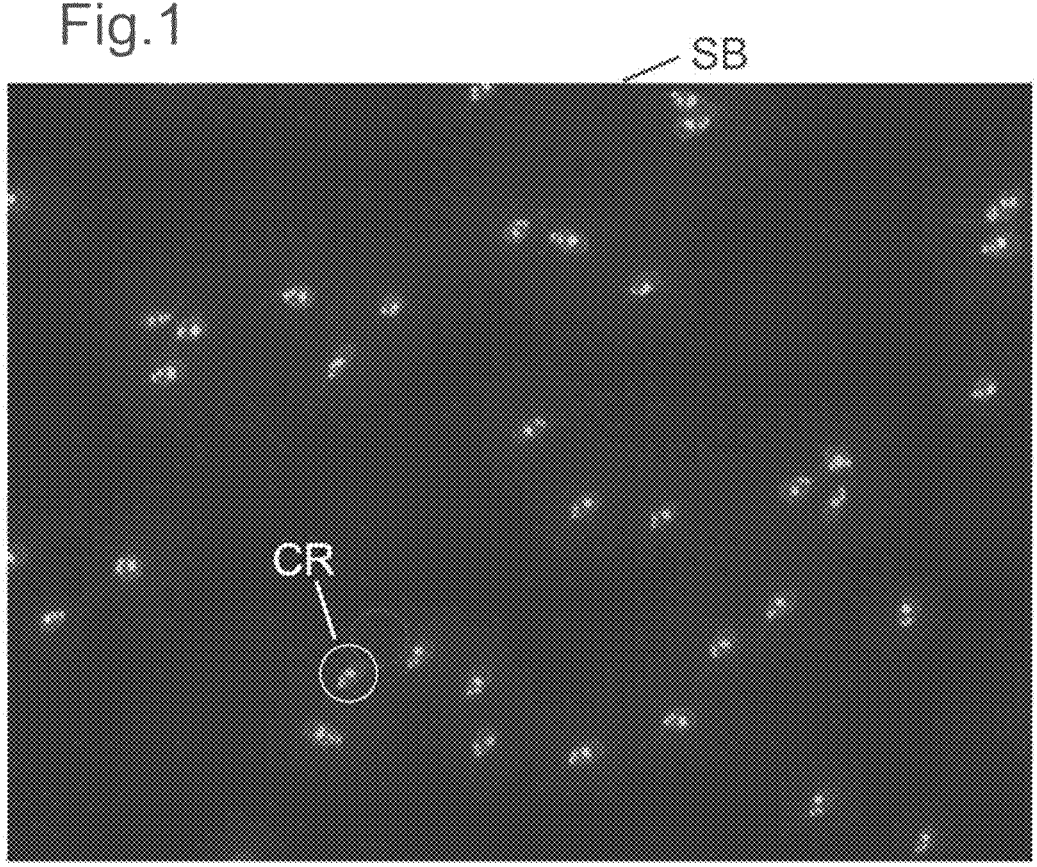
FIG. 1 shows a fluorescence image of a substrate having multiple *Crithidia luciliae* cells.

There is therefore proposed a method for detecting a binding of autoantibodies from a patient sample to double-stranded DNA using *Crithidia luciliae* cells by means of fluorescence microscopy and by means of digital image processing, which method comprises different steps. What takes place first of all is a provision of a substrate which has multiple *Crithidia luciliae* cells. The substrate is then incubated with the patient sample which potentially has the autoantibodies. Thereafter, the substrate is incubated with a first fluorescent dye, which preferably generates a staining in a red channel. Furthermore, the substrate is incubated with a conjugate, or rather secondary antibodies which have each been labelled with a second fluorescent dye, preferably a green fluorescent dye. Furthermore, what takes place is an acquisition of a first fluorescence image of the substrate in a first colour channel, preferably a red colour channel, which corresponds to the first fluorescent dye. The acquisition is preferably done by means of a fluorescence microscope. Furthermore, what takes place is an acquisition of a second fluorescence image of the substrate in a second colour channel, preferably a green colour channel, which corresponds to the second fluorescent dye. The acquisition is preferably done by means of the fluorescence microscope. What then takes place furthermore is an identification of respective first sub-images in the first fluorescence image, the first sub-images each representing at least one *Crithidia luciliae* cell. Furthermore, what takes place is a determination of respective second sub-images of the second fluorescence image that correspond to the respective first sub-images of the first fluorescence image. Furthermore, what takes place is a respective processing of at least one subset of the respective second sub-images by means of a pre-trained convolutional neural network (CNN) for determining respective binding measures. The respective binding measures indicate a respective extent of a respective binding of autoantibodies in a respective kinetoplast region of a respective *Crithidia luciliae* cell of a respective second sub-image. Lastly, what takes place is a determination of an overall binding measure with regard to the binding of autoantibodies from the patient sample to double-stranded DNA on the basis of the respective binding measures.

The patient sample is a liquid patient sample, preferably liquid blood or liquid blood constituents. More particularly, the liquid patient sample is liquid blood serum. Preferably, the patient sample has been diluted with so-called wash buffer, preferably so-called PBS Tween.

The conjugate has secondary antibodies which have been labelled with the second fluorescent dye.

The proposed method is especially a method for determining in vitro a presence of primary antibodies in a liquid patient sample.

The substrate is especially a biological sample which has animal-pathogenic hemoflagellates of the species *Crithidia luciliae*. These single-cell organisms have a double-stranded DNA-containing giant mitochondrion (kinetoplast) which has essentially none of the other antigens present in the nucleus. Primary autoantibodies from the patient sample that react with the kinetoplast are directed against dsDNA.

The fluorescence microscopy is especially a so-called indirect immunofluorescence microscopy (IIFT microscopy).

The substrate is preferably illuminated with excitation radiation in order to excite fluorescence radiation of the first and the second fluorescent dye. The excitation radiation is preferably a blue light and thus has wavelengths in a blue spectrum. Preferably, the excitation radiation is of an identical wavelength or an identical wavelength range for the first and also for the second fluorescent dye. The first fluorescent dye is preferably a red fluorescent dye, especially so-called Evans Blue (T-1824). The second fluorescent dye is preferably a green fluorescent dye, especially of the type fluorescein isothiocyanate (FITC).

To elucidate one or more possibly achievable advantages of the method according to the invention, more detailed information is provided below.

FIG. 7 shows a device V1, by means of which the method according to the invention can be carried out. The device V1 can be referred to as a fluorescence microscope. The device V1 comprises a mount H for a substrate S, which has been incubated in the manner stated above. Via an optics unit O, excitation light AL from an excitation light source LQ is guided towards the substrate S. Resultant fluorescence radiation FL is then split by means of further optical elements into different fluorescence radiations FL1 and FL2 in two different colour channels. A camera K1 is a first image acquisition unit and then acquires a first fluorescence image, especially in a red channel by means of a red filter FR A further camera K2 is a second image acquisition unit and then acquires a second fluorescence image of the substrate S in a second colour channel, especially a green channel by means of a green filter. The resultant fluorescence images are provided to a computing unit R as image information items BI1, BI2 and processed thereby. Preferably, there is only one single image acquisition unit, meaning that the single image acquisition unit acquires the differently stained fluorescence images of the different colour channels at different times by means of temporary exchange of the filters FR, FG.

Figure 3:
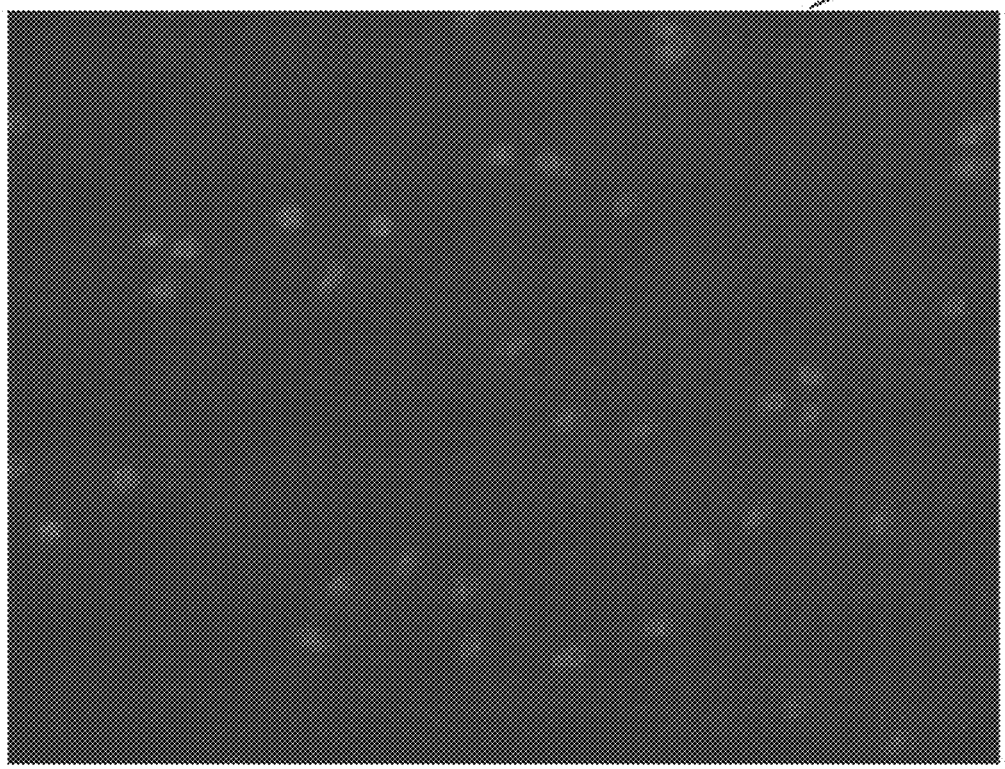
FIG. 3 shows a fluorescence image of the substrate in a first colour channel.
Figure 4:
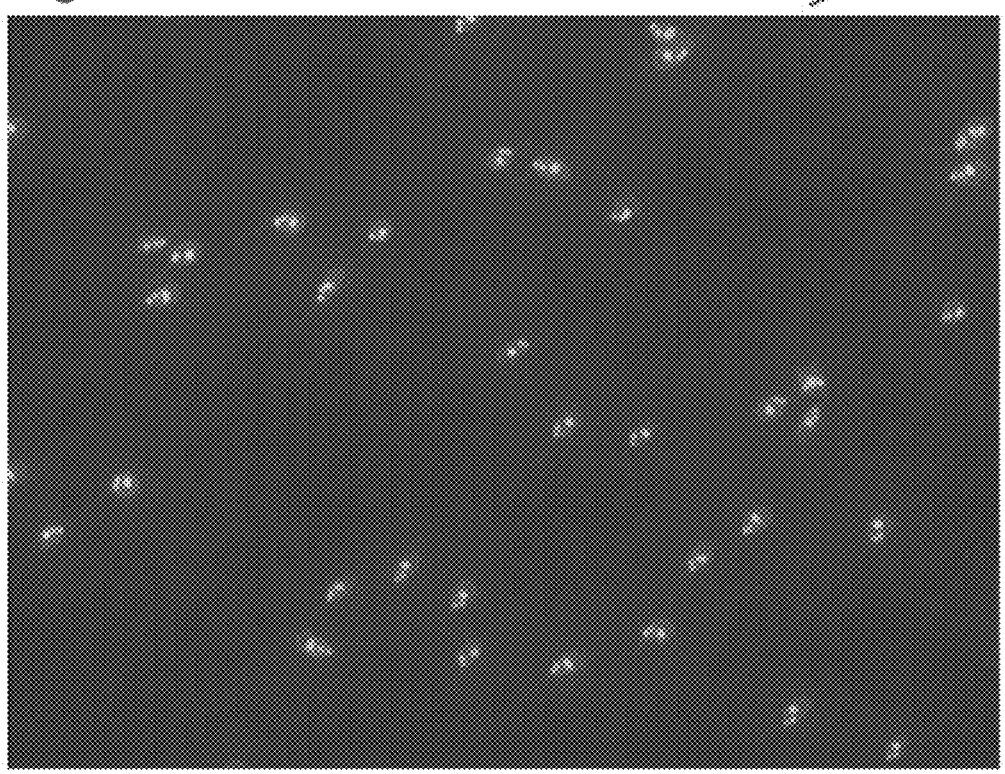
FIG. 4 shows a fluorescence image of the substrate in a second colour channel.

FIG. 3 shows an exemplary first fluorescence image SR from a red channel. FIG. 4 shows an exemplary second fluorescence image SG in a green channel.

Figure 5:
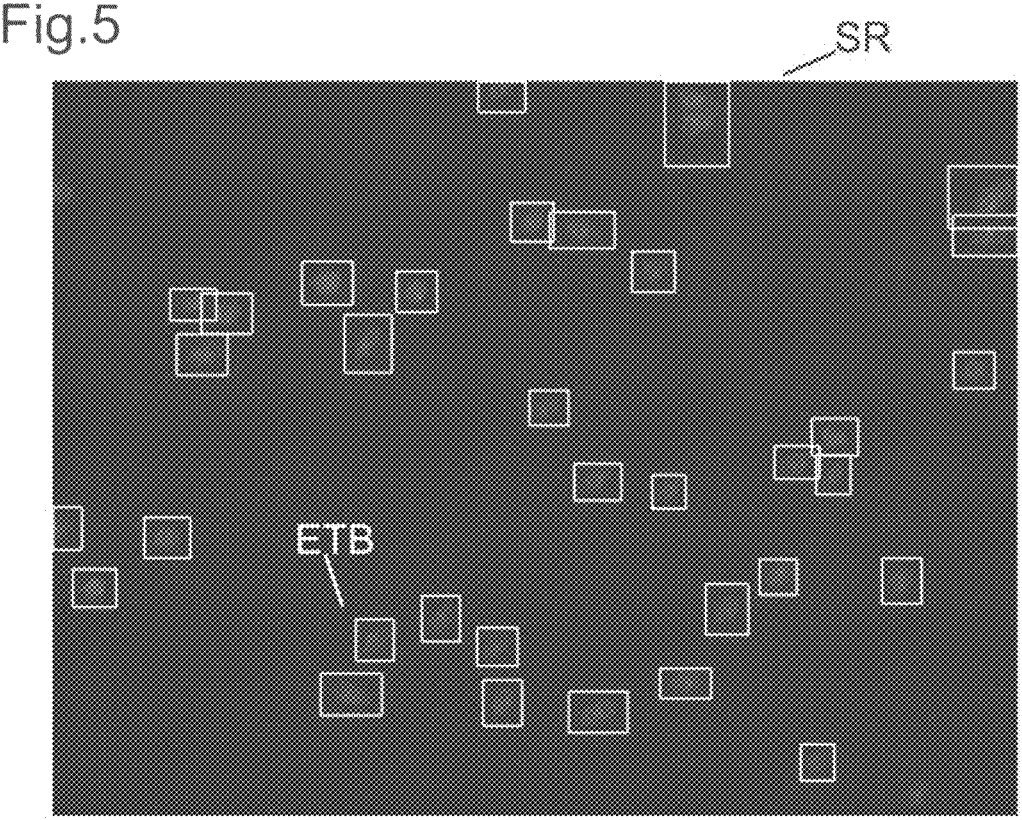
FIG. 5 shows the fluorescence image of the first colour channel with identified respective first sub-image regions.

According to the invention, what are identified first of all, on the basis of the first fluorescence image SR from FIG. 3, are first sub-images which have at least one *Crithidia luciliae* cell. In relation to this, FIG. 5 shows corresponding rectangle-labelled first sub-images and also a specific first sub-image region ETB.

Figure 6:
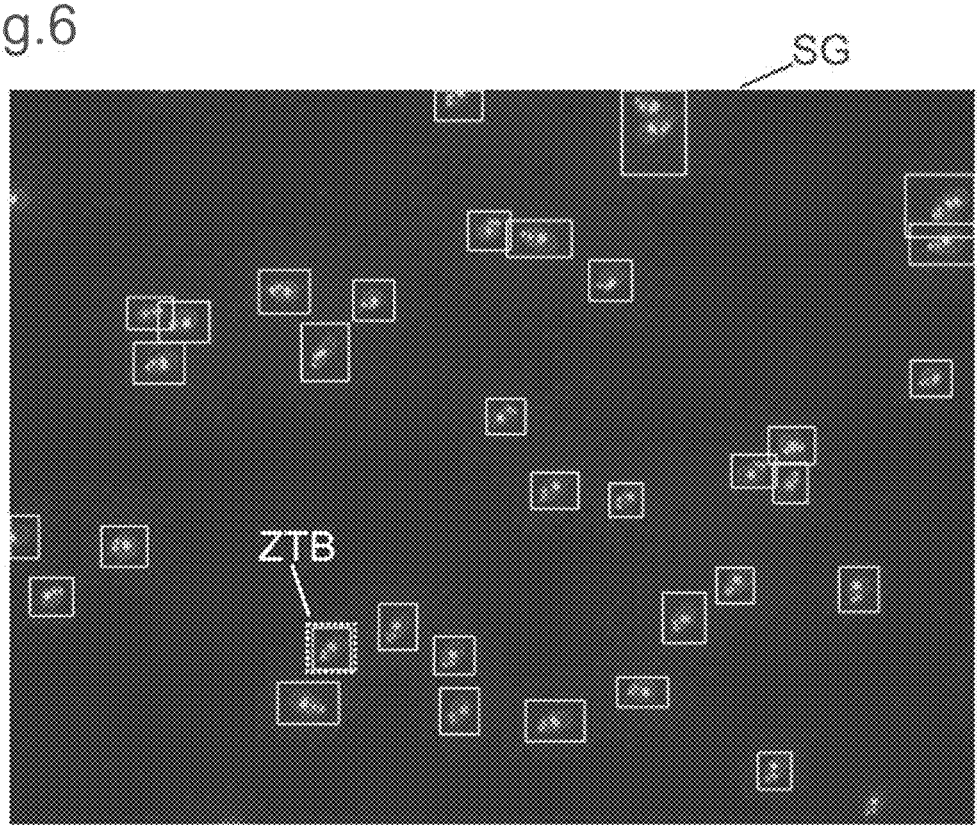
FIG. 6 shows the fluorescence image of the second colour channel with determined/identified respective second sub-image regions which correspond to the respective first sub-image regions of the first fluorescence image.

In relation to the second fluorescence image SG from FIG. 4. FIG. 6 shows respective second sub-images or second sub-image regions which correspond to the respective first sub-images of the first fluorescence image SR from FIG. 5. In particular, a specific second sub-image region ZTB corresponding to the specific first sub-image region ETB from FIG. 5 is depicted. In the context of this application, a sub-image region can also be referred to as a sub-image.

The second sub-image region ZTB from FIG. 6 is not absolutely identical to the first sub-image region ETB, but it corresponds thereto, since the same *Crithidia luciliae* cell is captured by said sub-image regions ETB, ZTB. If a first sub-image region or a first sub-image ETB in the first fluorescence image, as depicted in FIG. 5, has been determined, it is then possible to use the centre of said first sub-image region ETB and to place a corresponding second sub-image region ZTB of a predefined size around said centre in order to define the second sub-image region ZTB. In FIG. 6, the second sub-image region is entered by means of a dotted marking which illustrates the correspondence between the first sub-image region ETB from FIG. 5 and the second sub-image region ZTB from FIG. 6. Thus, the sub-image region ZTB need not be absolutely identical to the sub-image region ETB, but it can be.

Figure 2:
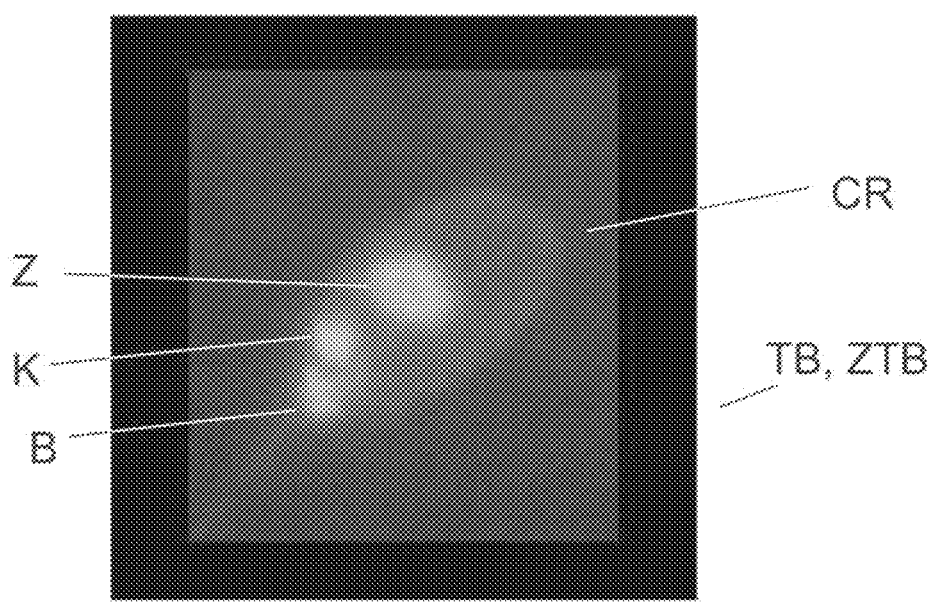
FIG. 2 shows a sub-image of the fluorescence image from FIG. 1 having one *Crithidia luciliae* cell.

Such an exemplary second sub-image ZTB is depicted in FIG. 2. As can be seen in FIG. 2, there can be up to three significantly stained regions in a *Crithidia luciliae* cell owing to a binding of antibodies, specifically in the region of the kinetoplast K, the basal body B and the nucleus Z. Therefore, it must be ensured that, in the fluorescence image SG of the second colour channel, any significant stainings are not used as assessment criterion, but only stainings of kinetoplast regions.

Figure 14A:
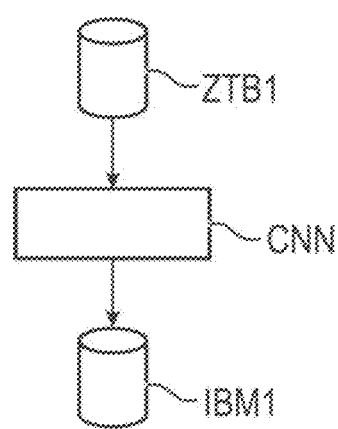
FIG. 14*a* shows a basic principle for ascertaining a binding measure of a binding of primary autoantibodies from the patient sample to a kinetoplast region for a second sub-image region.

FIG. 14a shows a further step of the method according to the invention, in which, for a specific second sub-image ZTB1, an associated binding measure IBM1 is determined by means of a convolutional neural network CNN. The binding measure IBM indicates an extent of a binding of autoantibodies in a kinetoplast region of the *Crithidia luciliae* cell depicted in the second sub-image.

Figure 14B:
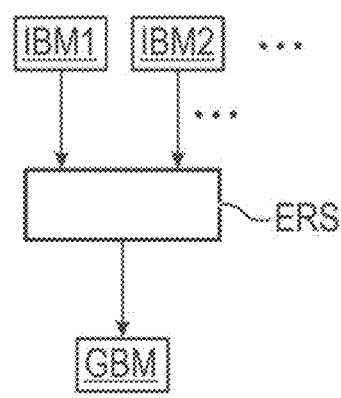
FIG. 14*b* shows a processing of multiple binding measures for determining an overall binding measure.

FIG. 14b illustrates a further step of the method according to the invention, in which different binding measures IBM1, IBM2 of different second sub-image regions are used as the basis to then ascertain an overall binding measure with regard to the detectable binding of autoantibodies from the patient sample to double-stranded DNA in the substrate.

Thus, the goal of the method according to the invention is a determination of the binding of the primary autoantibodies to the dsDNA in the respective kinetoplast regions of the respective *Crithidia luciliae* cells by means of determination of corresponding stainings of the corresponding kinetoplast regions by the second fluorescent dye in the corresponding second sub-image regions.

It should be stated that, in the method according to the invention, the entire fluorescence image of the second colour channel SG from FIG. 4 is not simply supplied to a convolutional neural network for an entire identification of multiple stained kinetoplast regions, but that instead the invention explicitly deviates from such a total classification approach for the entire second fluorescence image SG by means of a convolutional neural network. Specifically, according to the invention, what takes place first of all is a pre-processing such that the first sub-image regions are identified in the first fluorescence image in order to then cut out corresponding second sub-image regions in the second fluorescent dye image from FIG. 6, as illustrated by way of example for such a second sub-image region ZTB in FIG. 2. As can be seen in FIG. 2, there can be up to three significantly stained regions in a *Crithidia luciliae* cell owing to a binding of antibodies, specifically in the region of the kinetoplast K, the basal body B and the nucleus Z. Said second sub-image regions are then first each separately processed by the CNN in order to determine a respective subordinate image representing the kinetoplast region for a respective second sub-image and in order to then especially determine, by means of the subordinate image, a respective binding measure indicating a respective extent of a binding of autoantibodies in a respective kinetoplast region of a respective *Crithidia luciliae* cell of a respective second sub-image. In other words: said second sub-image regions in particular are first each separately processed by the CNN in order to identify a respective subordinate image for a respective second sub-image and in order to then determine, on the basis of the respective subordinate image, a respective binding measure for the respective second sub-image. Such a binding measure indicates a respective extent of a binding of autoantibodies in a respective kinetoplast region of a respective *Crithidia luciliae* cell of a respective second sub-image. These respective individual binding measures are used as the basis to then ascertain the overall binding measure.

As a result of the approach described here, the method according to the invention achieves a high degree of accuracy in the localization of the kinetoplast regions or in a detection of a colour change in the kinetoplast regions. If the entire fluorescence colour image of the second colour channel SG from FIG. 4 were to be supplied to a convolutional neural network in order to detect a colour change in a kinetoplast or in the various kinetoplast regions of the various *Crithidia luciliae* cells, other regions such as basal body regions or nucleus regions might be erroneously identified here as a kinetoplast region in each case and a determination of a binding of primary autoantibodies to dsDNA might therefore be distorted. Furthermore, a very large proportion of an entire fluorescence image SG of approx. 90% has merely background regions, meaning that, in the case of a processing of an entire fluorescence image SG by a CNN, the image pixels belonging to the background region would also have to be processed, which would make the CNN very complicated and a processing inefficient. Furthermore, from the entire fluorescence image SG, the CNN would also additionally have to identify those subordinate regions which each represent a kinetoplast, which is complicated owing to possible stainings of nucleus regions or basal body regions. Specifically, a staining of a kinetoplast region does not necessarily have to be present in the event of a staining of a basal body region and/or a nucleus region. Different positions of the *Crithidia luciliae* cells within the substrate or the fluorescence colour image of the second colour channel SG, as depicted in FIG. 4, mean as well that there are simply too many degrees of freedom for a reliable classification of individual image segments as kinetoplast by a convolutional neural network.

Instead of a processing of an entire second fluorescence image by a CNN, what takes place according to the invention is a separate processing by the CNN for a respective second sub-image which has a respective *Crithidia luciliae* cell. The position of the second sub-image with regard to the entire second fluorescence image is simply determined on the basis of an evaluation of the first fluorescence image. What is made possible thereby is that the CNN can be explicitly trained on individual second sub-images, i.e. on respective second sub-images having individual *Crithidia luciliae* cells. The CNN then only has to detect the position of the kinetoplast in this second sub-image. Said position can simply be preferably determined as a so-called subordinate image. With regard to the individual kinetoplast, it is then possible to determine a binding measure for this cell or this kinetoplast by the CNN.

In other words: according to the invention, what is made possible by supplying only determined individual second sub-image regions in each case into the convolutional neural network is that the convolutional neural network is limited merely to an analysis of such a second sub-image or an individual depiction of an individual *Crithidia luciliae* cell in order to identify the kinetoplast and to determine the binding measure with regard to the autoantibodies. If an entire fluorescence colour image like the image SG from FIG. 4 were to be supplied to a convolutional neural network for a classification task for detecting different kinetoplasts in the course of a training phase, said convolutional neural network would have to be configured very largely in terms of its degree of freedom and it would be very complicated and inefficient to train such a CNN. Since the convolutional neural network according to the invention has to process in each case only an individual second sub-image region separately in order to then determine a corresponding binding measure, the convolutional neural network can be limited to a processing of an image representing a *Crithidia luciliae* cell, as depicted in FIG. 2.

Advantageous embodiments of the invention are subject matter of the dependent claims and are more particularly elucidated in the following description with reference in some cases to the figures.

Preferably, the method comprises, for a respective second sub-image, the steps of: selection of a respective subordinate image of the respective second sub-image, the respective subordinate image representing a respective kinetoplast region of a respective *Crithidia luciliae* cell, furthermore determination of the respective binding measure on the basis of the respective subordinate image. The method preferably comprises furthermore: determination of the overall binding measure on the basis of the respective binding measures.

Preferably, the method comprises the steps of: determination of at least one respective final feature map for a respective second sub-image by means of the convolutional neural network, furthermore determination of a respective confidence measure with regard to a presence of a binding of autoantibodies in a respective kinetoplast region for the respective second sub-image or for a respective final feature map, especially on the basis of the respective final feature map, furthermore selection of a subset of the second sub-images or selection of a subset of the respective final feature maps on the basis of the determined confidence measures, furthermore respective processing of the respective feature maps of the respective selected second sub-images for determining the respective binding measures. The method preferably comprises furthermore: determination of the overall binding measure on the basis of the respective binding measures.

Preferably, the method comprises, for a respective second sub-image from the selected subset, the steps of: selection of a respective subordinate image of the respective second sub-image on the basis of the respective final feature map corresponding to the respective second sub-image, the respective subordinate image representing a respective kinetoplast region of a respective *Crithidia luciliae* cell, and furthermore determination of the respective binding measure on the basis of the respective subordinate image. The method preferably comprises furthermore: determination of the overall binding measure on the basis of the respective binding measures.

Preferably, the method comprises, for a respective second sub-image from the selected subset, furthermore the steps of: ascertainment of a respective masking operator on the basis of the respective final feature map, furthermore selection of the respective subordinate image of the respective second sub-image by means of application of the respective masking operator to the respective second sub-image, furthermore determination of the respective binding measure on the basis of the respective subordinate image. The method preferably comprises furthermore: determination of the overall binding measure on the basis of the respective binding measures.

Preferably, the method is configured such that, in the course of a processing of a second sub-image, the convolutional neural network, in a first processing level, generates a first set of resultant feature maps on the basis of the second sub-image by means of a first convolutional layer, furthermore in a second processing level, generates a second set of resultant feature maps on the basis of the first set of two-dimensional feature maps by means of a second convolutional layer and furthermore generates a third set of resultant feature maps on the basis of the second set of two-dimensional feature maps by means of a third convolutional layer, wherein the second set has a smaller number of resultant feature maps than the first set and the third set has a larger number of resultant feature maps than the second set.

Preferably, the method is configured such that the second convolutional layer and the third convolutional layer are in a sequence as sub-steps of a sequential processing path, wherein, in the second processing level, there is in parallel to the sequential processing path a further processing path in which the convolutional neural network generates a fourth set of resultant feature maps on the basis of the first set of two-dimensional feature maps by means of at least one fourth convolutional layer, wherein, furthermore, the convolutional neural network generates on the basis of the third and the fourth set of resultant feature maps the final feature map corresponding to the second sub-image and wherein, furthermore, the number of successive convolution layers in the parallel processing path is smaller than the number of successive convolution layers in the sequential processing path.

Preferably, the method comprises the steps of: acquisition of a first preliminary fluorescence image in the first colour channel using a predefined acquisition parameter, determination of a brightness value indicating a brightness of the first preliminary fluorescence image of the first colour channel, modification of the acquisition parameter depending on the determined brightness value, acquisition of a second preliminary fluorescence image in the first colour channel using the modified acquisition parameter and, furthermore, use of the second preliminary fluorescence image of the first colour channel as the first fluorescence image of the first colour channel.

Preferably, the method comprises the steps of: acquisition of a first preliminary fluorescence image in the first colour channel using a predefined acquisition parameter, determination of a brightness value indicating a brightness of the first preliminary fluorescence image of the first colour channel, establishment by means of the brightness value as to whether a brightness of the first preliminary fluorescence image of the first colour channel corresponds to an expected brightness, in the event of the brightness of the first preliminary fluorescence image of the first colour channel corresponding to the expected brightness, use of the first preliminary fluorescence image of the first colour channel as the first fluorescence image of the first colour channel, in the event of the brightness of the first preliminary fluorescence image not corresponding to the expected brightness, modification of the acquisition parameter depending on the determined brightness value, acquisition of a second preliminary fluorescence image in the first colour channel using the modified acquisition parameter, use of the second preliminary fluorescence image of the first colour channel as the first fluorescence image of the first colour channel.

Preferably, the method comprises the steps of: acquisition of a first preliminary fluorescence image in the second colour channel using a predefined acquisition parameter, establishment of whether a brightness of the first preliminary fluorescence image of the second colour channel exceeds a maximum brightness, in the event of the first preliminary fluorescence image of the second colour channel not exceeding the maximum brightness, use of the first preliminary fluorescence image as the second fluorescence image of the second colour channel, in the event of the first preliminary fluorescence image of the second colour channel exceeding the maximum brightness, acquisition of a second preliminary fluorescence image in the second colour channel and use of the second preliminary fluorescence image of the second colour channel as the second fluorescence image of the second colour channel.

There is furthermore proposed a device according to the invention for detecting a binding of autoantibodies from a patient sample to double-stranded deoxyribonucleic acid using *Crithidia luciliae* cells by means of fluorescence microscopy and by means of digital image processing, comprising a mounting device for a substrate which has multiple *Crithidia luciliae* cells and which has been incubated with a patient sample having the autoantibodies, with a first fluorescent dye and, furthermore, with secondary antibodies which have each been labelled with a second fluorescent dye. The device comprises furthermore at least one image acquisition unit for acquiring a first fluorescence image of the substrate in a first colour channel and, furthermore, for acquiring a second fluorescence image of the substrate in a second colour channel. The device comprises furthermore at least one computing unit which is designed to identify respective first sub-images in the first fluorescence image that each represent at least one *Crithidia luciliae* cell, furthermore to determine respective second sub-images of the second fluorescence image that correspond to the respective first sub-images of the first fluorescence image, furthermore to respectively process at least one subset of the respective second sub-images by means of a pretrained convolutional neural network for determining respective binding measures which indicate a respective extent of a binding of autoantibodies in a respective kinetoplast region of a respective *Crithidia luciliae* cell of a respective second sub-image, and furthermore to determine an overall binding measure of a binding of autoantibodies from the patient sample to double-stranded deoxyribonucleic acid on the basis of the respective binding measures.

There is furthermore proposed a computing unit which is designed, in the course of a digital image processing, to receive a first fluorescence image which represents a staining of a substrate, which in turn has multiple *Crithidia luciliae* cells, by a first fluorescent dye and to receive a second fluorescence image which represents a staining of the substrate by a second fluorescent dye, furthermore to identify respective first sub-images in the first fluorescence image that each represent at least one *Crithidia luciliae* cell, furthermore to determine respective second sub-images of the second fluorescence image that correspond to the respective first sub-images of the first fluorescence image, furthermore to respectively process at least one subset of the respective second sub-images by means of a pretrained convolutional neural network for determining respective binding measures which indicate a respective extent of a binding of autoantibodies in a respective kinetoplast region of a respective *Crithidia luciliae* cell of a respective second sub-image, and furthermore to determine an overall binding measure of a binding of autoantibodies from the patient sample to double-stranded deoxyribonucleic acid on the basis of the respective binding measures.

There is furthermore proposed a data network device comprising at least one data interface for receiving a first fluorescence image which represents a staining of a substrate, which in turn has multiple *Crithidia luciliae* cells, by a first fluorescent dye and, furthermore, for receiving a second fluorescence image which represents a staining of the substrate by a second fluorescent dye. The data network device comprises furthermore a computing unit which is designed, in the course of a digital image processing, to identify respective first sub-images in the first fluorescence image that each represent at least one *Crithidia luciliae* cell, furthermore to determine respective second sub-images of the second fluorescence image that correspond to the respective first sub-images of the first fluorescence image, furthermore to respectively process at least one subset of the respective second sub-images by means of a pretrained convolutional neural network for determining respective binding measures which indicate a respective extent of a binding of autoantibodies in a respective kinetoplast region of a respective *Crithidia luciliae* cell of a respective second sub-image, and furthermore to determine an overall binding measure of a binding of autoantibodies from the patient sample to double-stranded deoxyribonucleic acid on the basis of the respective binding measures.

There is furthermore proposed a method for digital image processing, comprising the steps of: receiving of a first fluorescence image which represents a staining of a substrate, which in turn has multiple *Crithidia luciliae* cells, by a first fluorescent dye and, furthermore, of a second fluorescence image which represents a staining of the substrate by a second fluorescent dye, furthermore identification of respective first sub-images in the first fluorescence image that each represent at least one *Crithidia luciliae* cell, furthermore determination of respective second sub-images of the second fluorescence image that correspond to the respective first sub-images of the first fluorescence image, furthermore respective processing of at least one subset of the respective second sub-images by means of a pretrained convolutional neural network for determining respective binding measures which indicate a respective extent of a binding of autoantibodies in a respective kinetoplast region of a respective *Crithidia luciliae* cell of a respective second sub-image, and furthermore determination of an overall binding measure of a binding of autoantibodies from the patient sample to double-stranded deoxyribonucleic acid on the basis of the respective binding measures.

There is furthermore proposed a computer program product comprising commands which, upon the execution of the program by a computer, prompt said computer to carry out the method according to the invention for digital image processing.

There is furthermore proposed a data carrier signal which transmits the proposed computer program product.

Without restriction of the general concept of the invention, the invention is more particularly elucidated below on the basis of specific embodiments with reference to the figures, where:

FIG. 1 shows a fluorescence image of a substrate having multiple *Crithidia luciliae* cells, FIG. 2 shows a sub-image of the fluorescence image from FIG. 1 having one *Crithidia luciliae* cell, FIG. 3 shows a fluorescence image of the substrate in a first colour channel.

FIG. 4 shows a fluorescence image of the substrate in a second colour channel,

FIG. 5 shows the fluorescence image of the first colour channel with identified respective first sub-image regions.

Figure 11C:
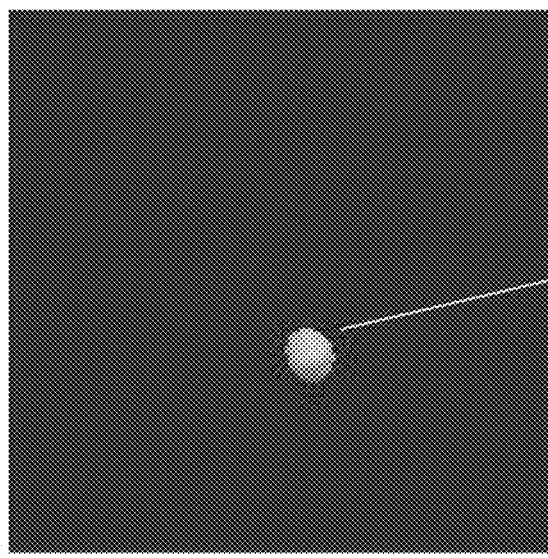
FIG. 11*c* shows a selected subordinate-image region of a subordinate image from the second sub-image region from FIG. 10*a*.
Figure 11B:
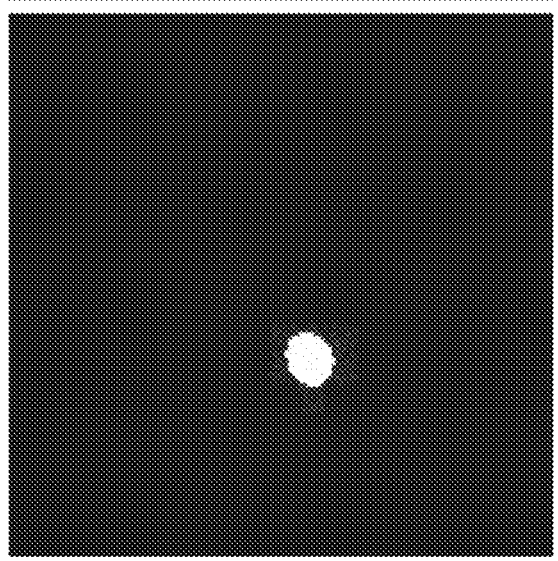
FIG. 11*b* shows a binary-value masking operator derived from the interpolated feature map from FIG. 11*a*.
Figure 11A:
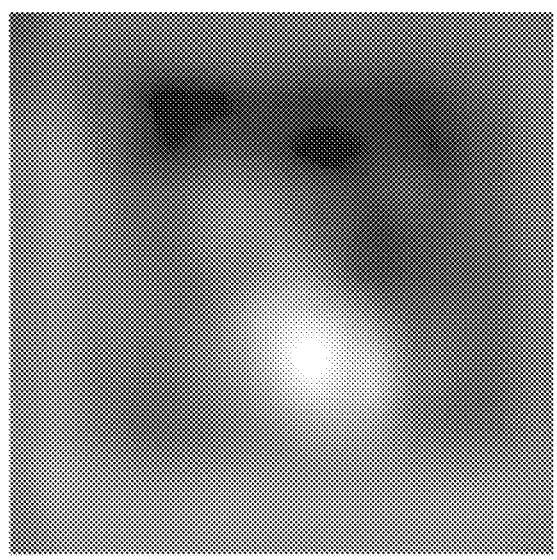
FIG. 11*a* shows an interpolated version of the first final feature map from FIG. 10*b*.

FIG. 6 shows the fluorescence image of the second colour channel with determined/identified respective second sub-image regions which correspond to the respective first sub-image regions of the first fluorescence image, FIG. 7 shows an exemplary embodiment of the device according to the invention, FIG. 8 shows a modified version of the fluorescence image of the first colour channel with increase in contrast, FIG. 9 shows a binary-value image derived from the contrast-increased fluorescence image from FIG. 8, FIG. 10a shows an exemplary second sub-image, FIG. 10b shows a first final feature map, FIG. 10c shows a second final feature map to be preferably determined, FIG. 11a shows an interpolated version of the first final feature map from FIG. 10b, FIG. 11b shows a binary-value masking operator derived from the interpolated feature map from FIG. 11a, FIG. 11c shows a selected subordinate-image region of a subordinate image from the second sub-image region from FIG. 10a.

Figure 12B:
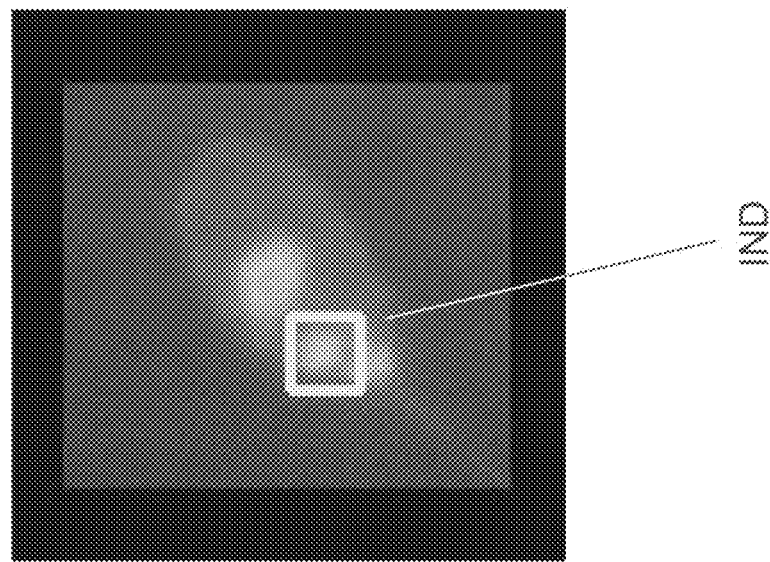
FIG. 12*b* shows a depiction of an indicated image region in the second sub-image region that corresponds to the subordinate image from FIG. 11*c*.
Figure 13:
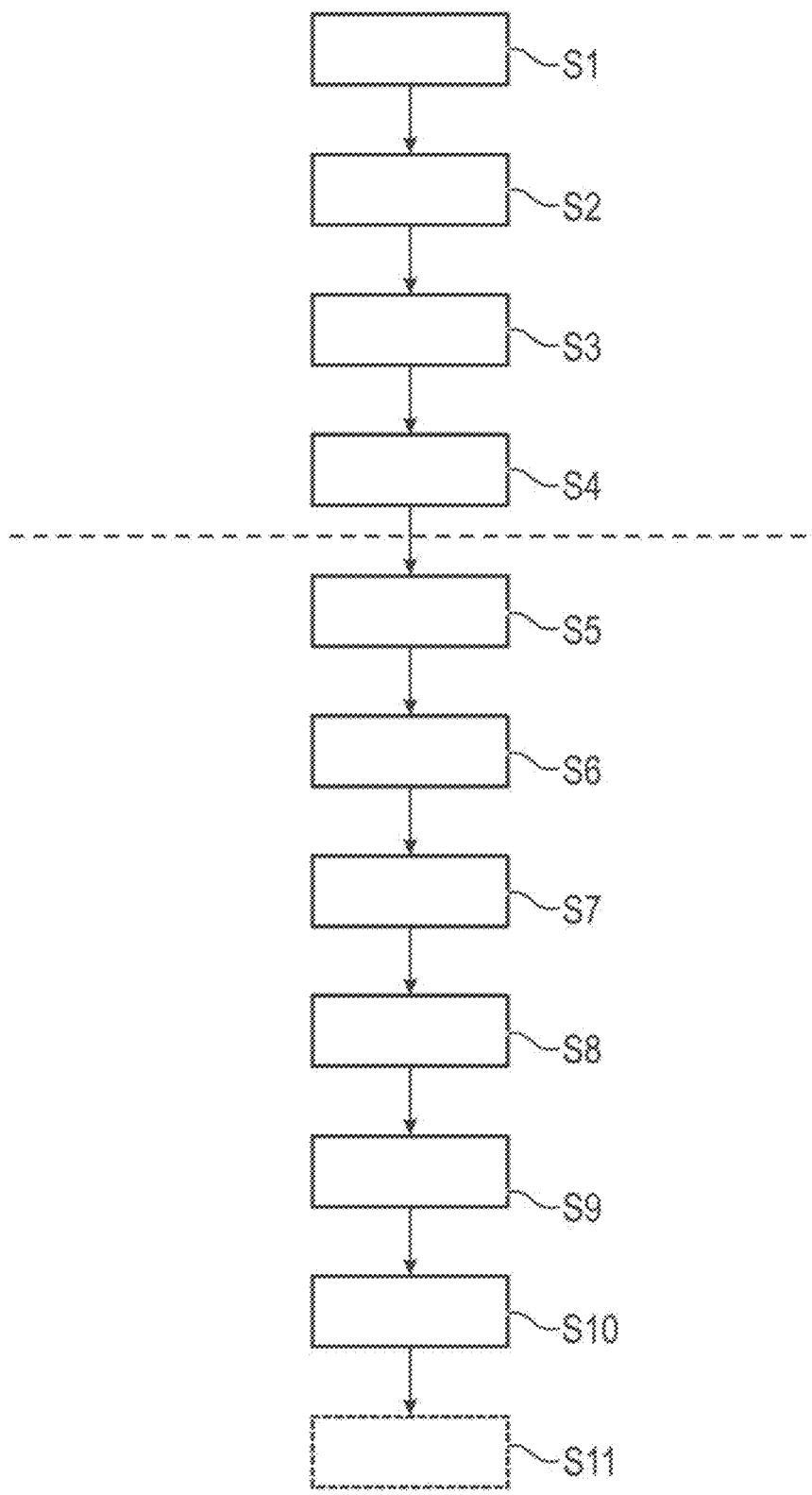
FIG. 13 shows steps for carrying out the method according to the invention.
Figure 15:
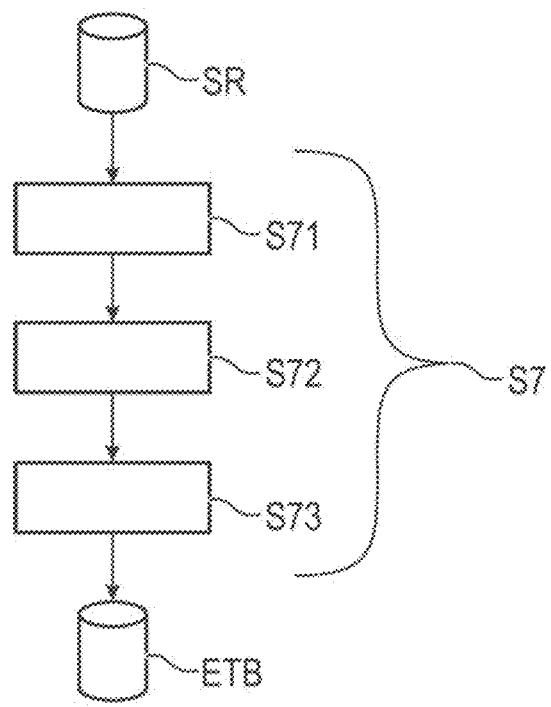
FIG. 15 shows sub-steps for determining first sub-image regions in the first fluorescence colour image of the first colour channel.
Figure 16A:
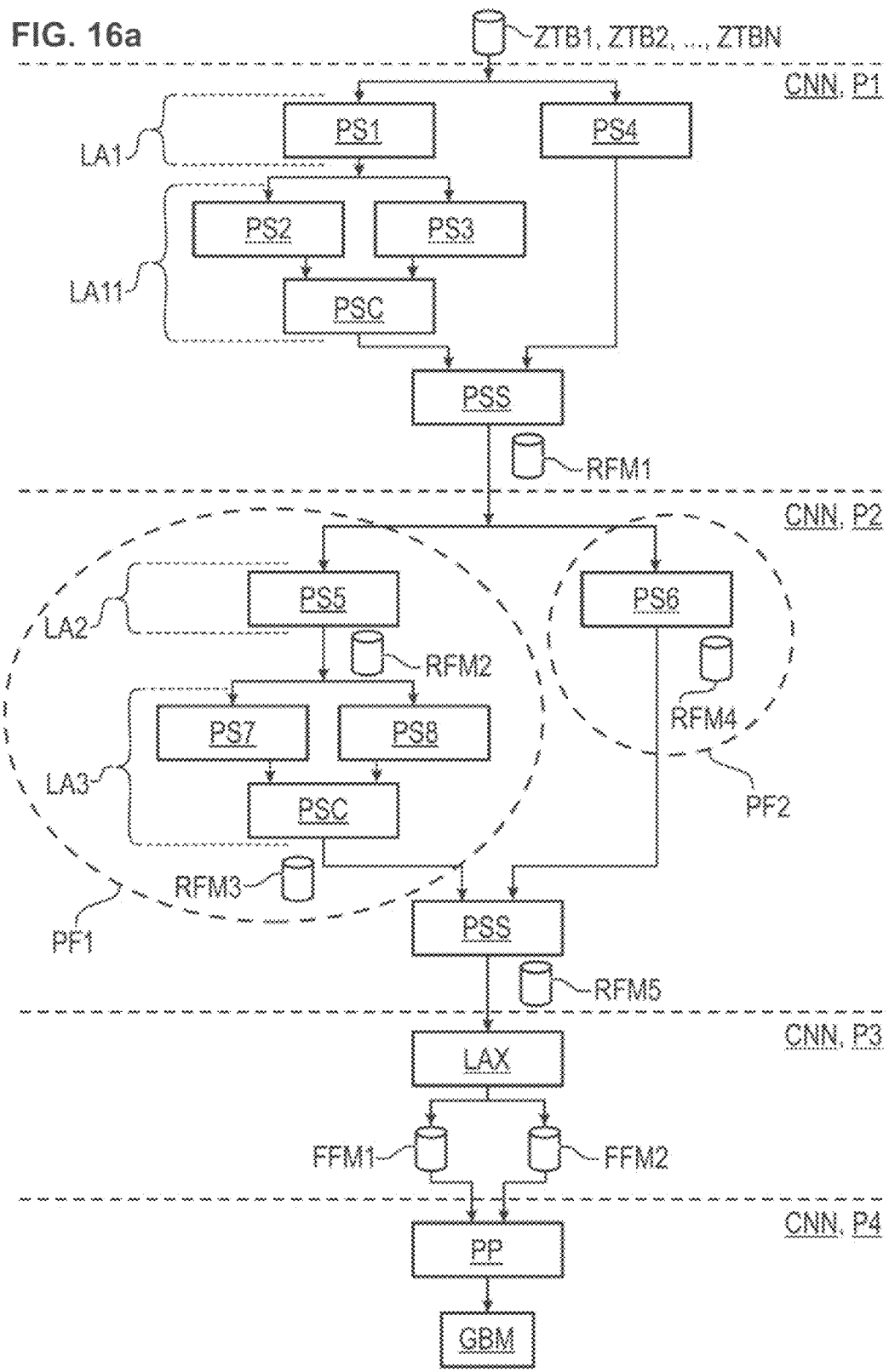
FIG. 16*a* shows an exemplary illustration of a preferred embodiment of a convolutional neural network.
Figure 16B:
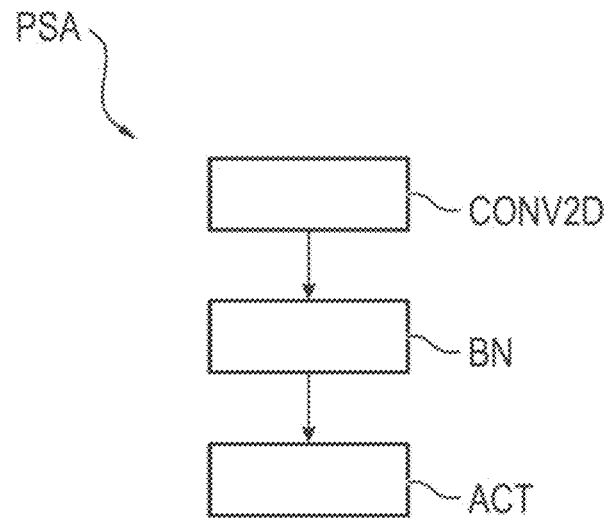
FIG. 16*b* shows sub-steps of a first type of a convolutional layer of the convolutional neural network.
Figure 16C:
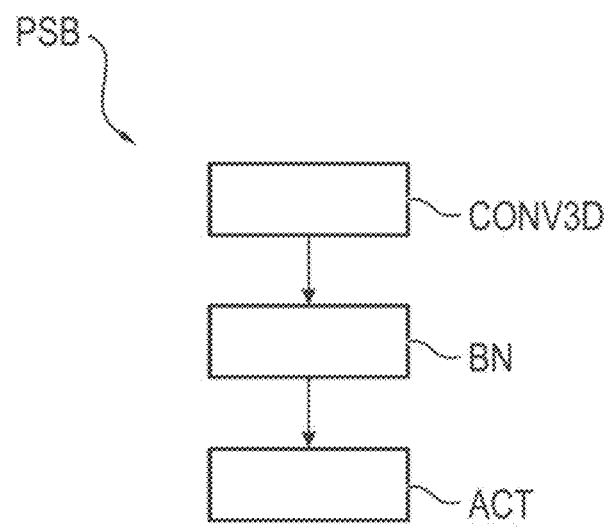
FIG. 16*c* shows sub-steps of a further type of a convolutional layer of the convolutional neural network.
Figure 17:
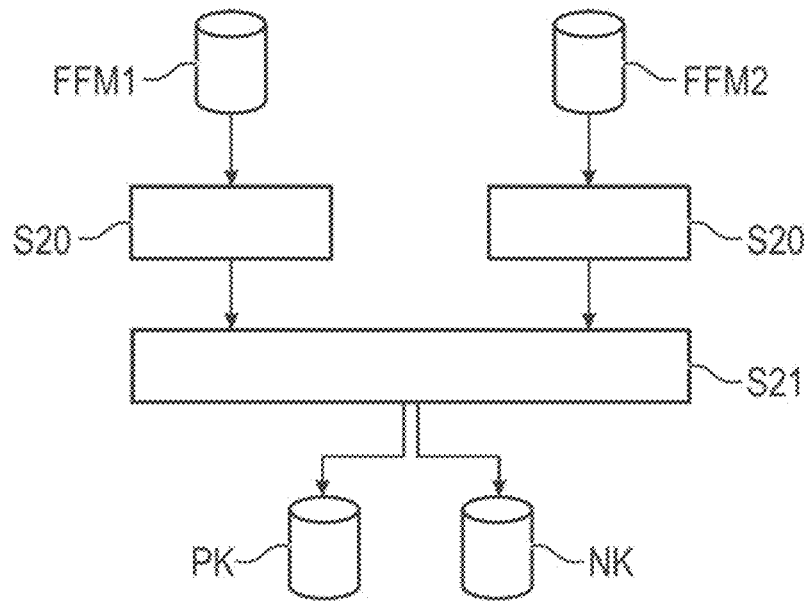
FIG. 17 shows processing steps for determining a confidence measure with regard to a presence of a binding of autoantibodies to a kinetoplast region for a corresponding second sub-image on the basis of the associated feature maps.
Figure 18:
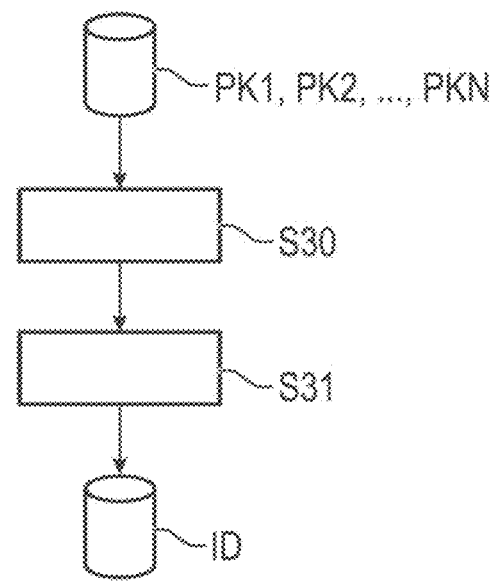
FIG. 18 shows steps for selecting a subset of the second sub-images on the basis of the confidence measures of the respective second sub-images.
Figure 19:
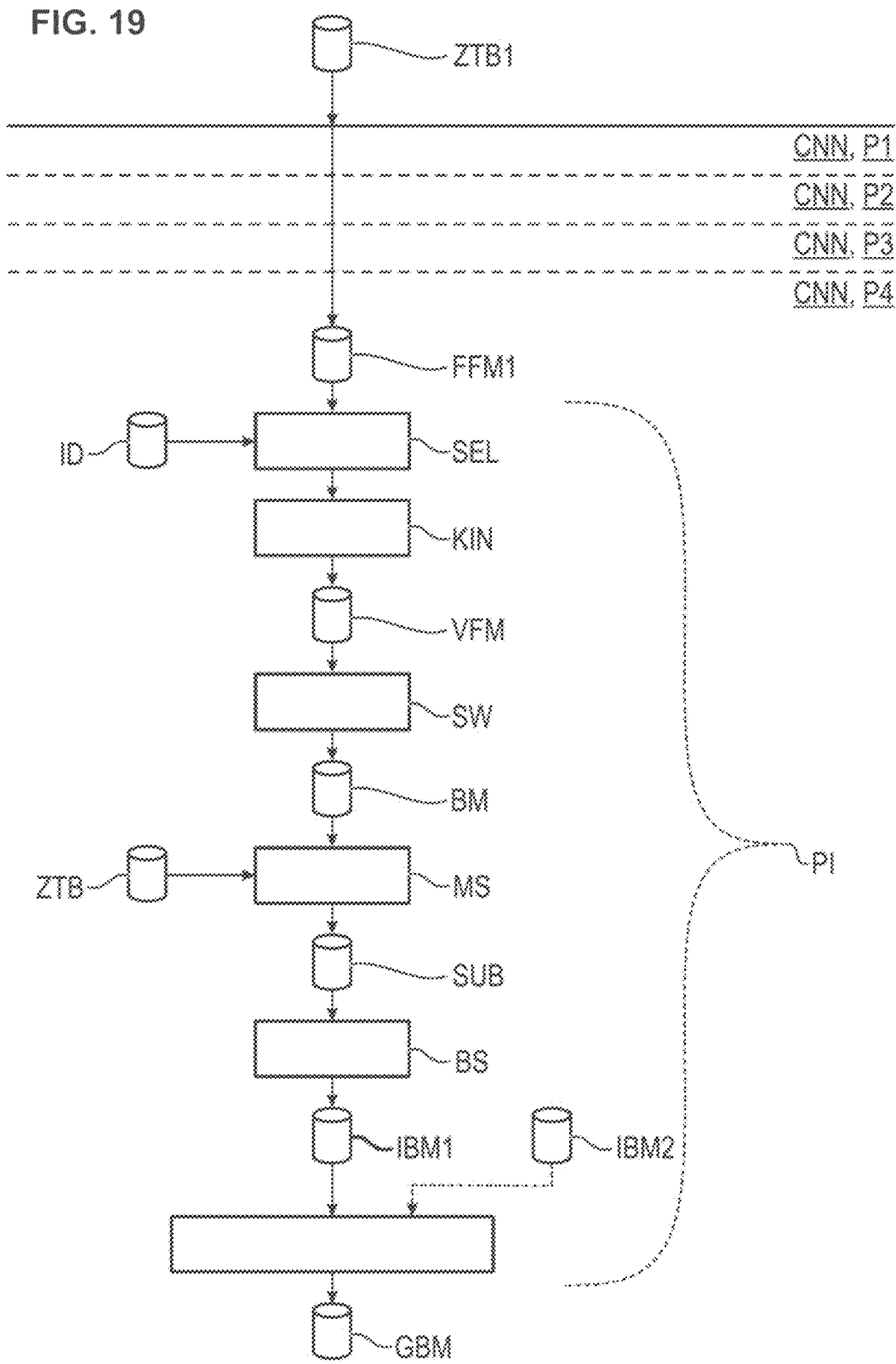
FIG. 19 shows steps for a selection of a respective subordinate image of a respective second sub-image and for a determination of a respective binding measure on the basis of the respective subordinate image by means of application of a binary-value masking operator to the respective second sub-image.
Figure 20:
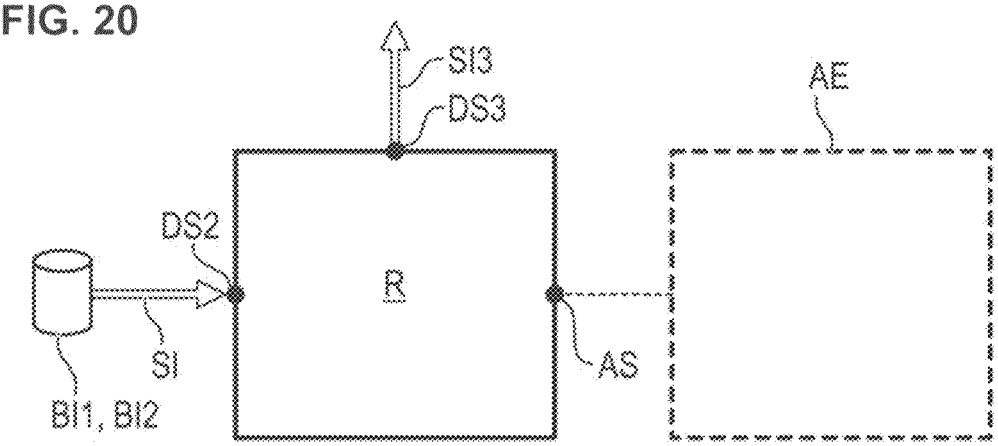
FIG. 20 shows an exemplary depiction of a computing unit according to the invention.
Figure 21:
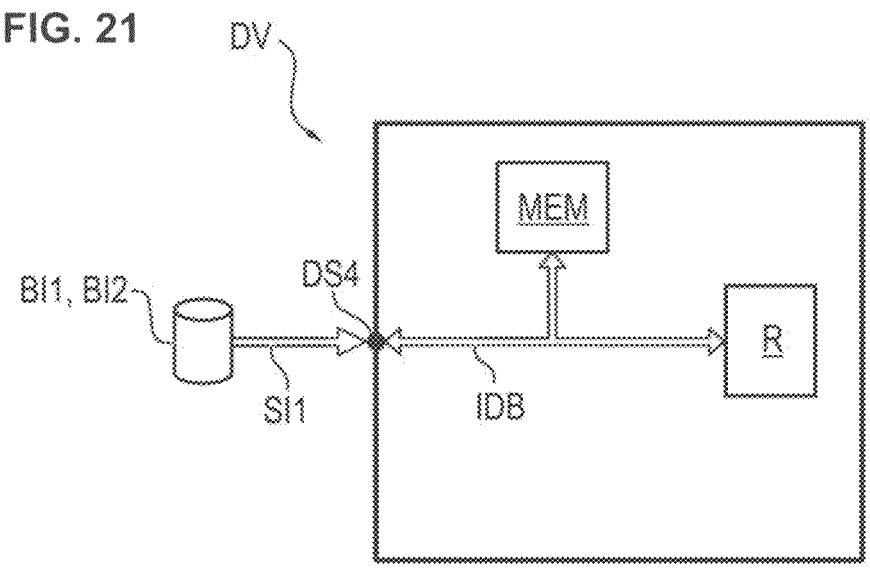
FIG. 21 shows an exemplary depiction of a data network device according to the invention.
Figure 22:
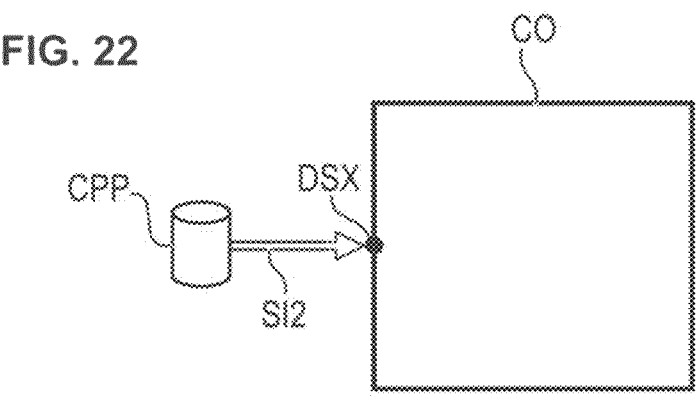
FIG. 22 shows an exemplary depiction of a computer program product according to the invention and of a data carrier signal according to the invention.
Figure 23:
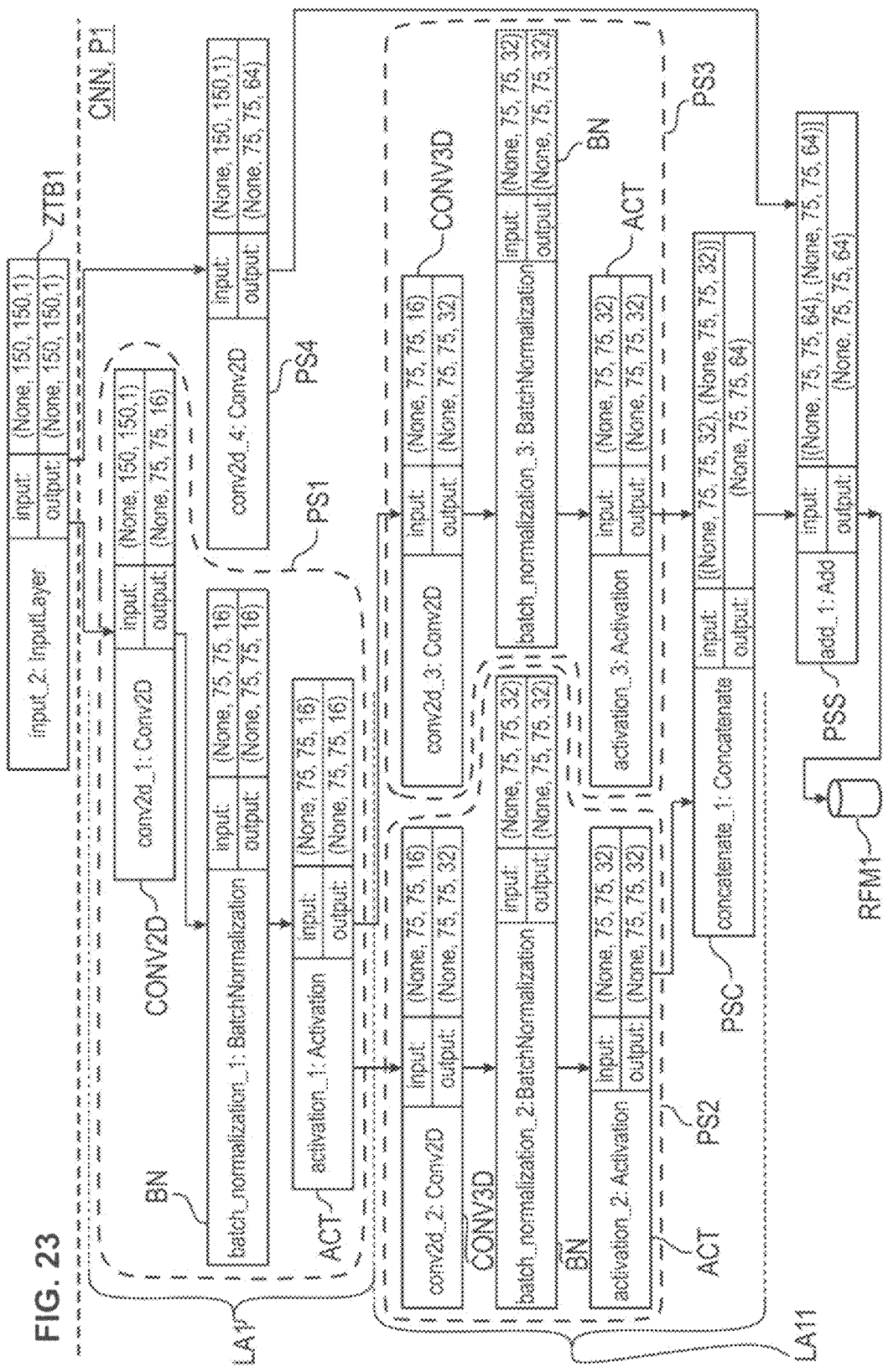
FIG. 23 shows an exemplary embodiment of a first processing level of the CNN.
Figure 24:
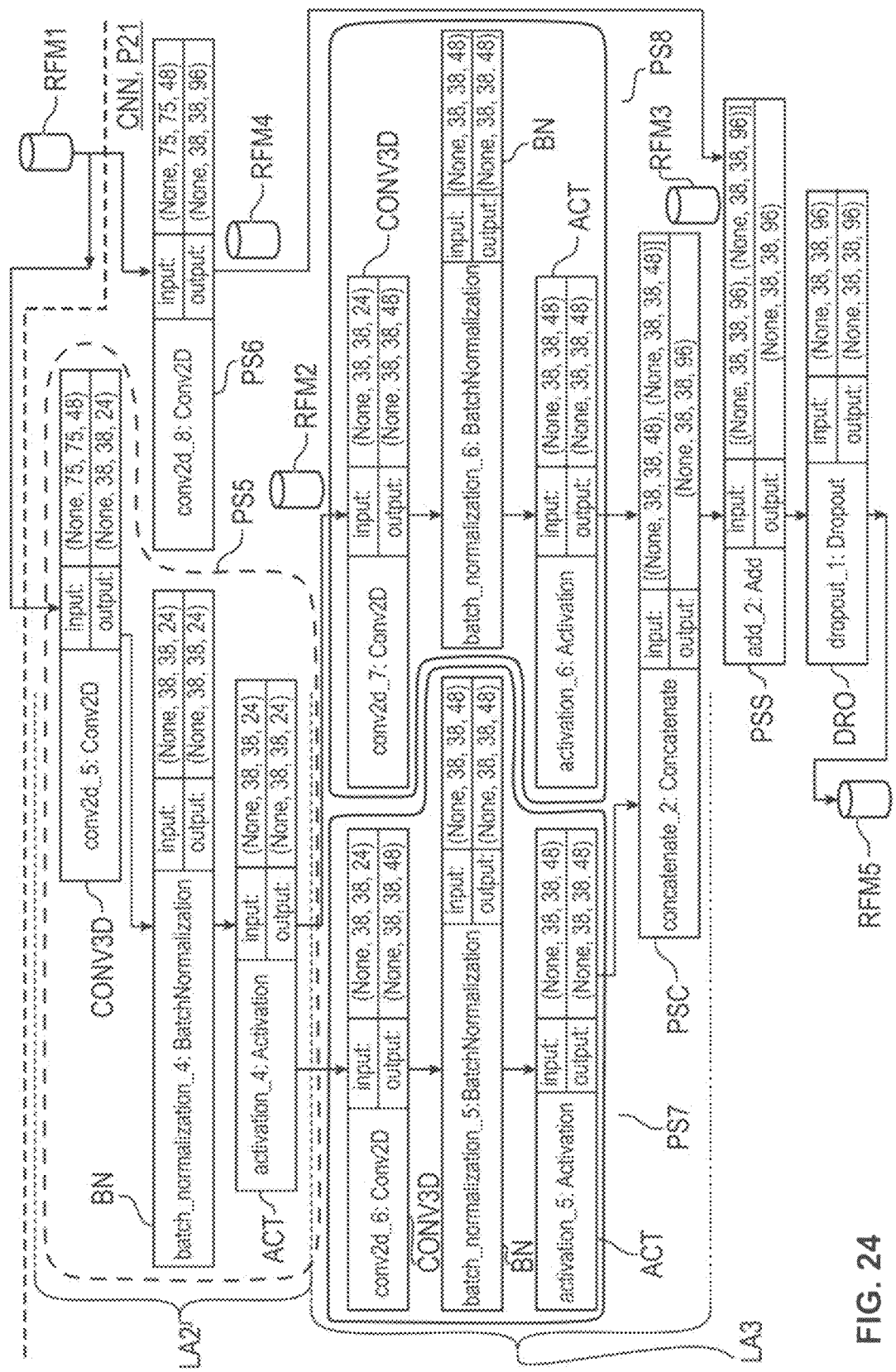
FIG. 24 shows an exemplary embodiment of a first part of a second processing level of the CNN.
Figure 25:
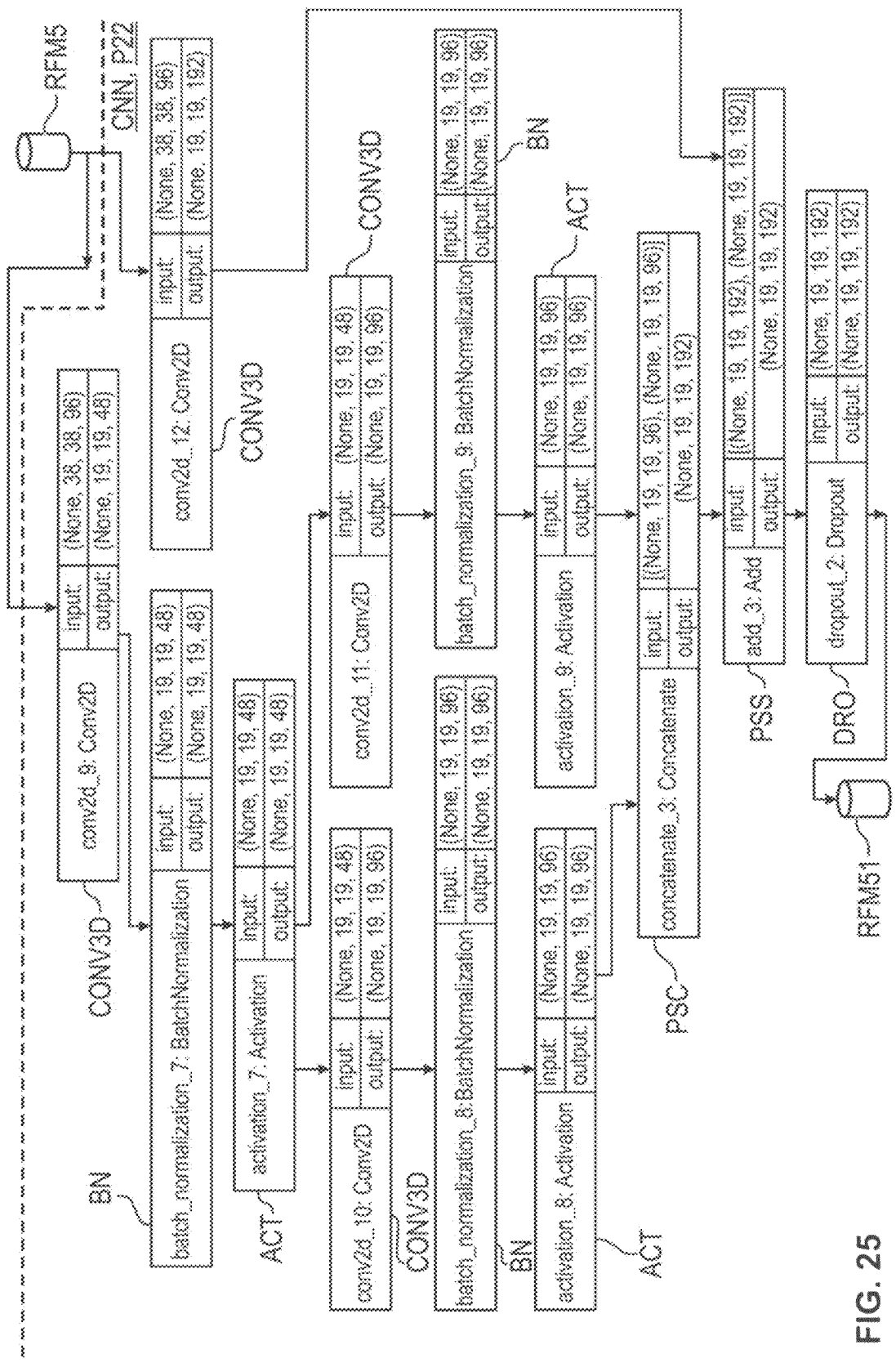
FIG. 25 shows an exemplary embodiment of a second part of a second processing level of the CNN.
Figure 26:
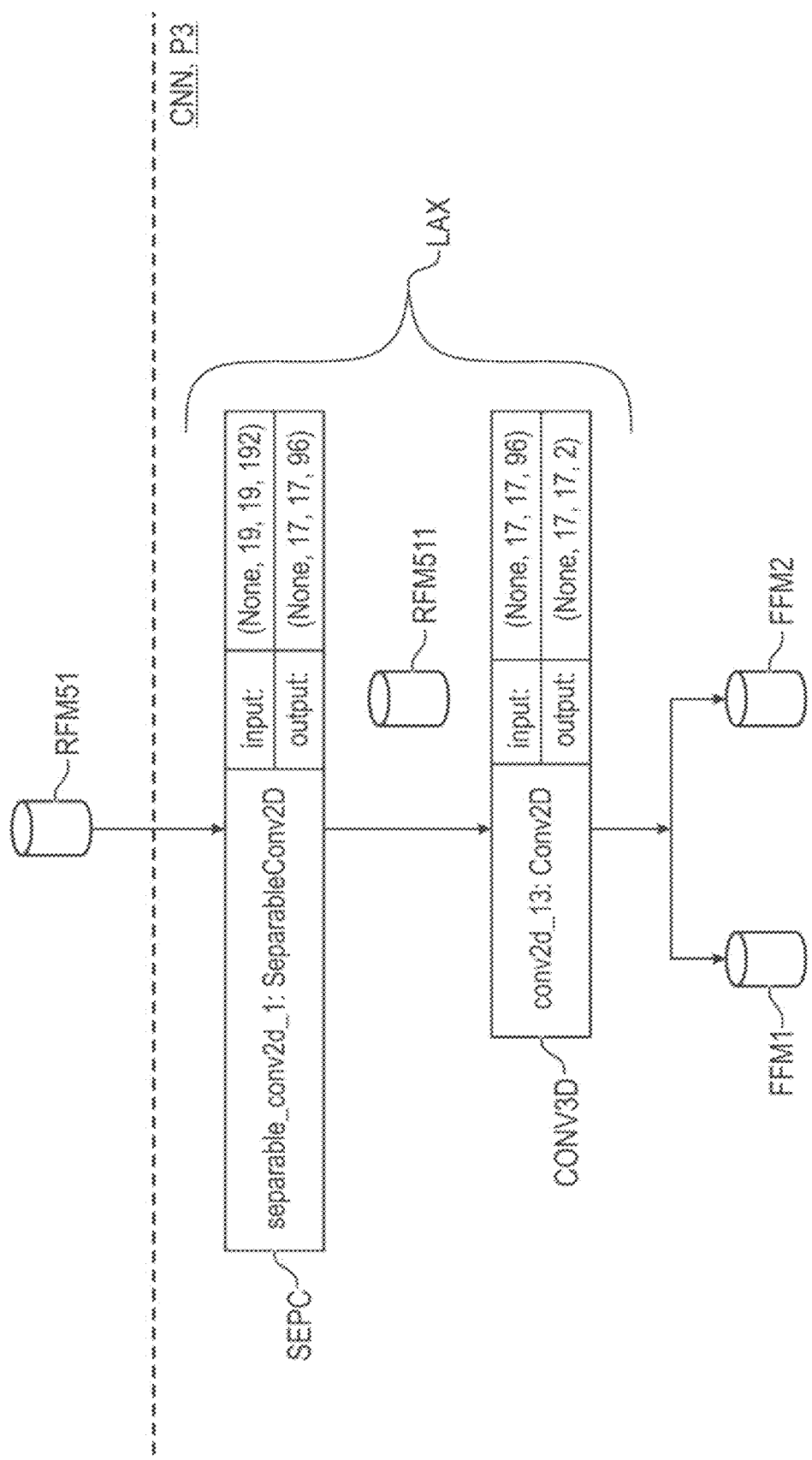
FIG. 26 shows an exemplary embodiment of a third processing level of the CNN.

FIG. 12a shows again the second sub-image,

FIG. 12b shows a depiction of an indicated image region in the second sub-image region that corresponds to the subordinate image from FIG. 11c, FIG. 13 shows steps for carrying out the method according to the invention, FIG. 14a shows a basic principle for ascertaining a binding measure of a binding of primary autoantibodies from the patient sample to a kinetoplast region for a second sub-image region, FIG. 14b shows a processing of multiple binding measures for determining an overall binding measure, FIG. 15 shows sub-steps for determining first sub-image regions in the first fluorescence colour image of the first colour channel, FIG. 16a shows an exemplary illustration of a preferred embodiment of a convolutional neural network, FIG. 16b shows sub-steps of a first type of a convolutional layer of the convolutional neural network, FIG. 16c shows sub-steps of a further type of a convolutional layer of the convolutional neural network, FIG. 17 shows processing steps for determining a confidence measure with regard to a presence of a binding of autoantibodies to a kinetoplast region for a corresponding second sub-image on the basis of the associated feature maps, FIG. 18 shows steps for selecting a subset of the second sub-images on the basis of the confidence measures of the respective second sub-images, FIG. 19 shows steps for a selection of a respective subordinate image of a respective second sub-image and for a determination of a respective binding measure on the basis of the respective subordinate image by means of application of a binary-value masking operator to the respective second sub-image, FIG. 20 shows an exemplary depiction of a computing unit according to the invention, FIG. 21 shows an exemplary depiction of a data network device according to the invention, FIG. 22 shows an exemplary depiction of a computer program product according to the invention and of a data carrier signal according to the invention, FIG. 23 shows an exemplary embodiment of a first processing level of the CNN, FIG. 24 shows an exemplary embodiment of a first part of a second processing level of the CNN, FIG. 25 shows an exemplary embodiment of a second part of a second processing level of the CNN, FIG. 26 shows an exemplary embodiment of a third processing level of the CNN.

Figure 27:
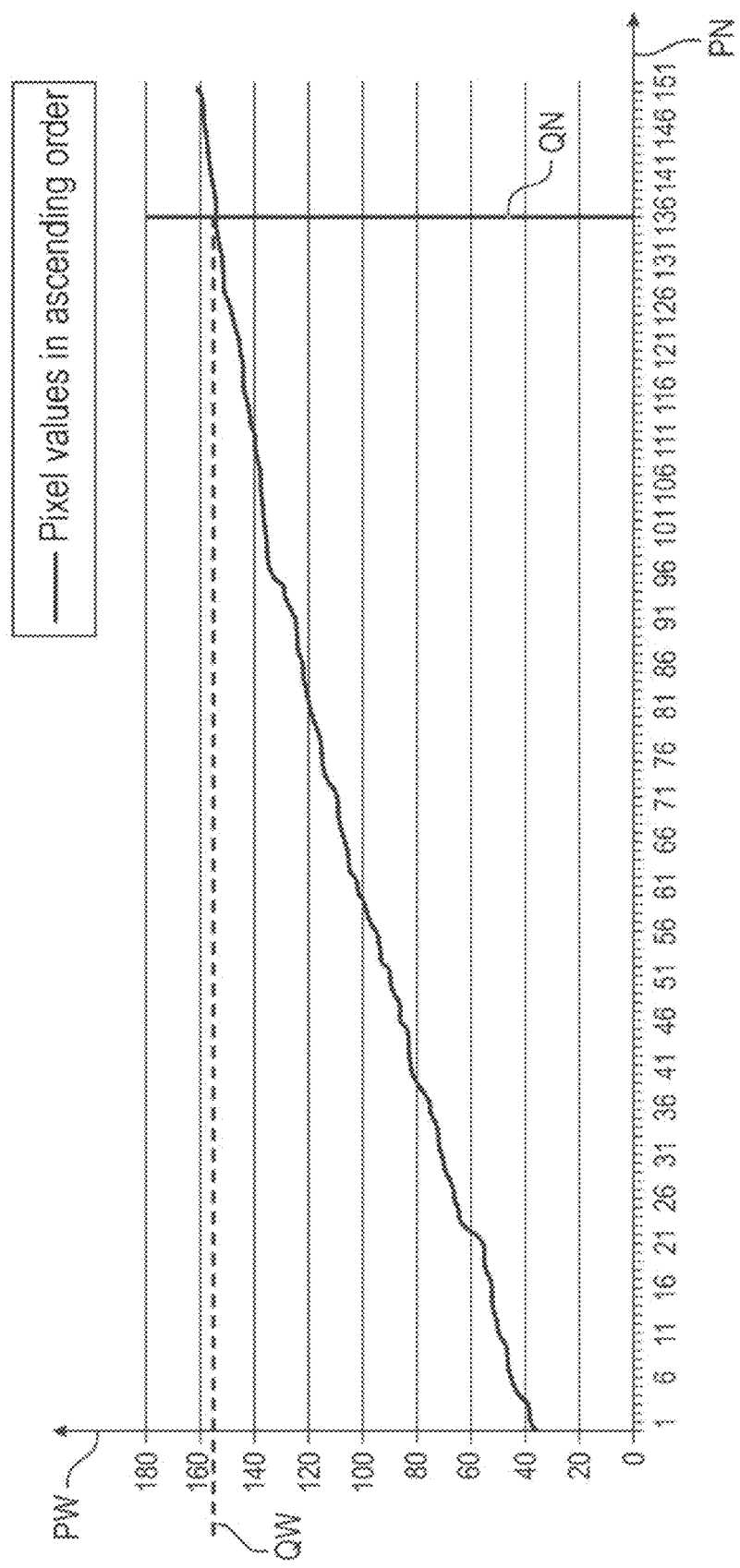
FIG. 27 shows pixel values of a subordinate image.
Figure 28:
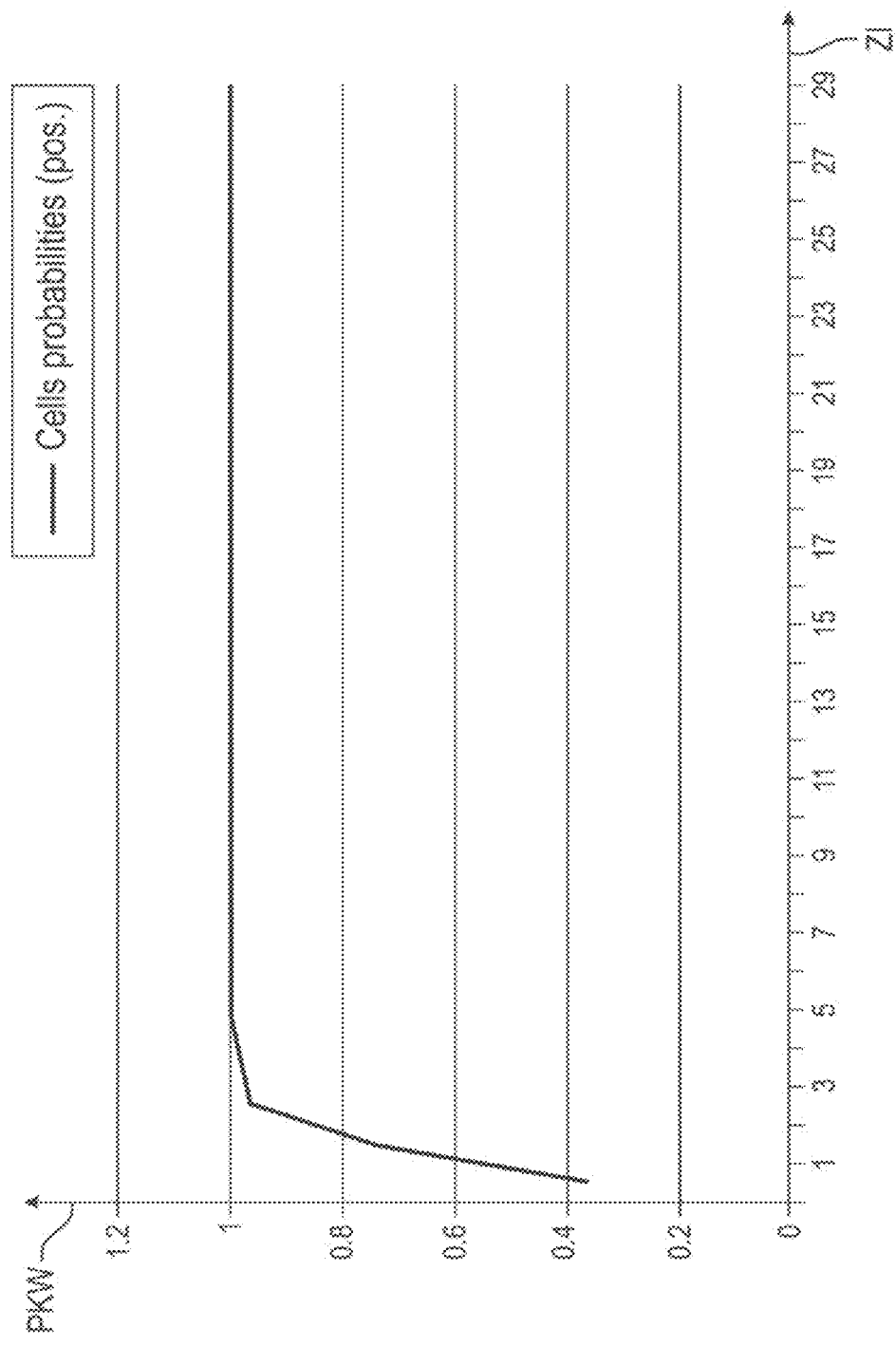
FIG. 28 shows respective confidence measure values for respective second sub-images of a second fluorescence image.
Figure 29:
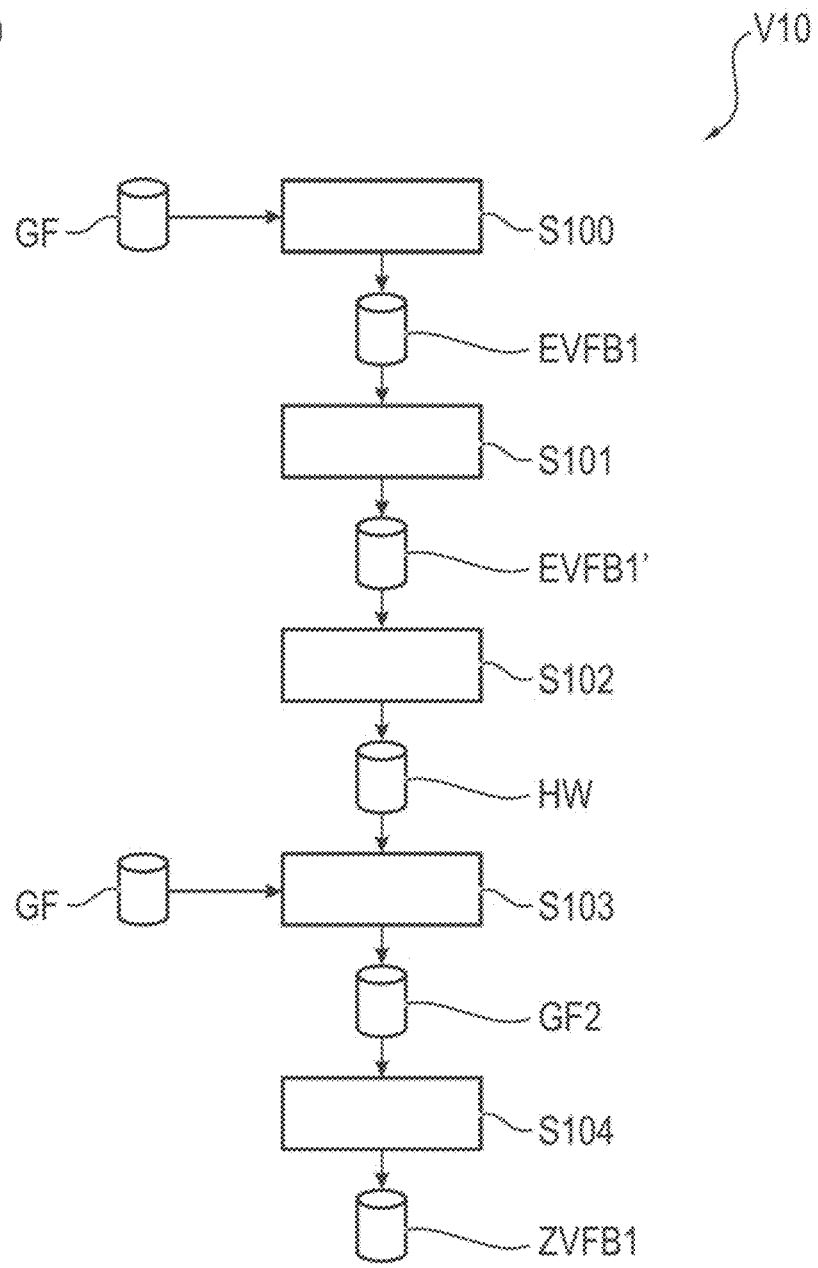
FIG. 29 shows steps of a method for an acquisition of a first fluorescence image according to a preferred first embodiment.
Figure 30:
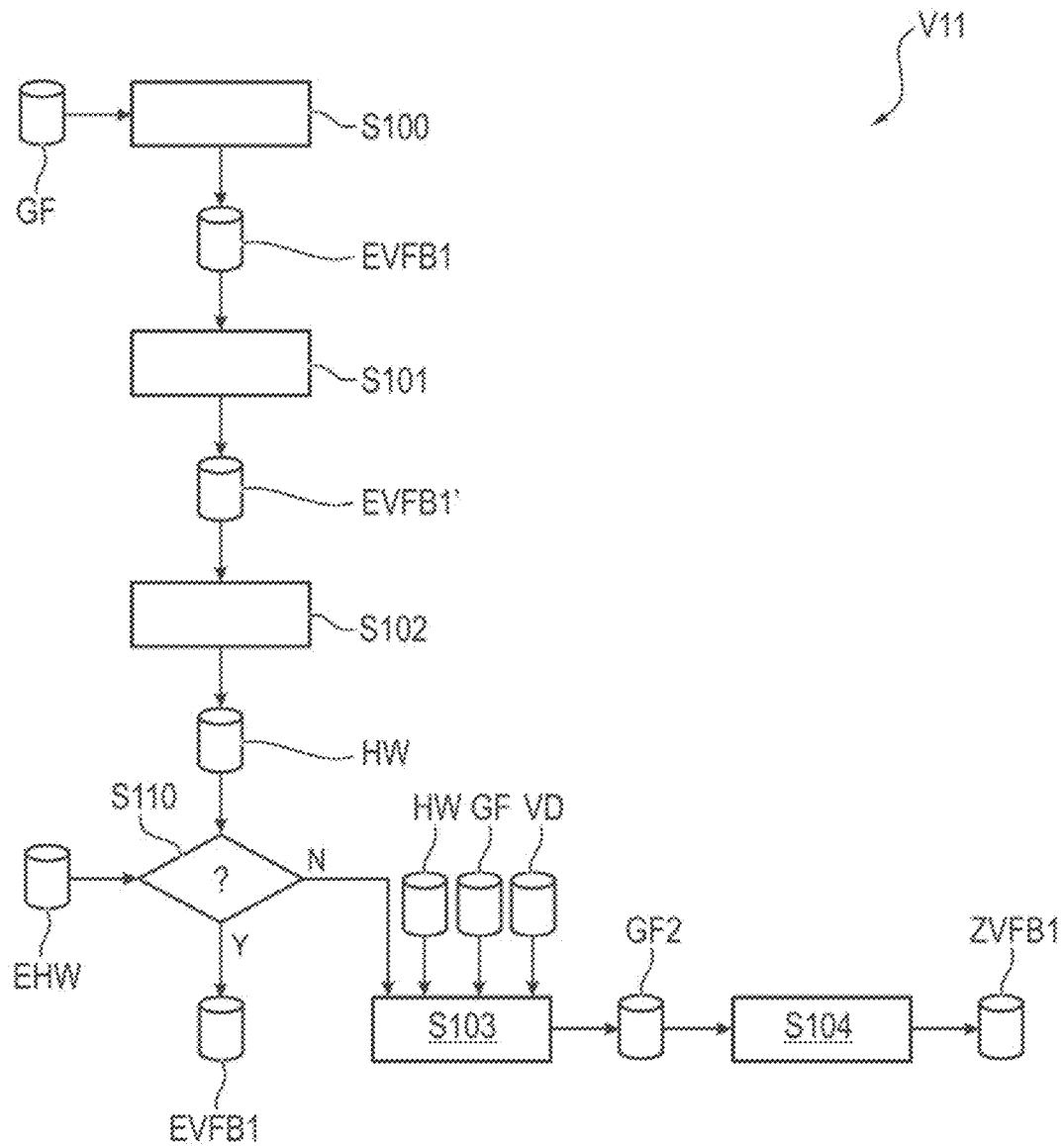
FIG. 30 shows steps of a method for an acquisition of a first fluorescence image according to a preferred second embodiment.
Figure 31:
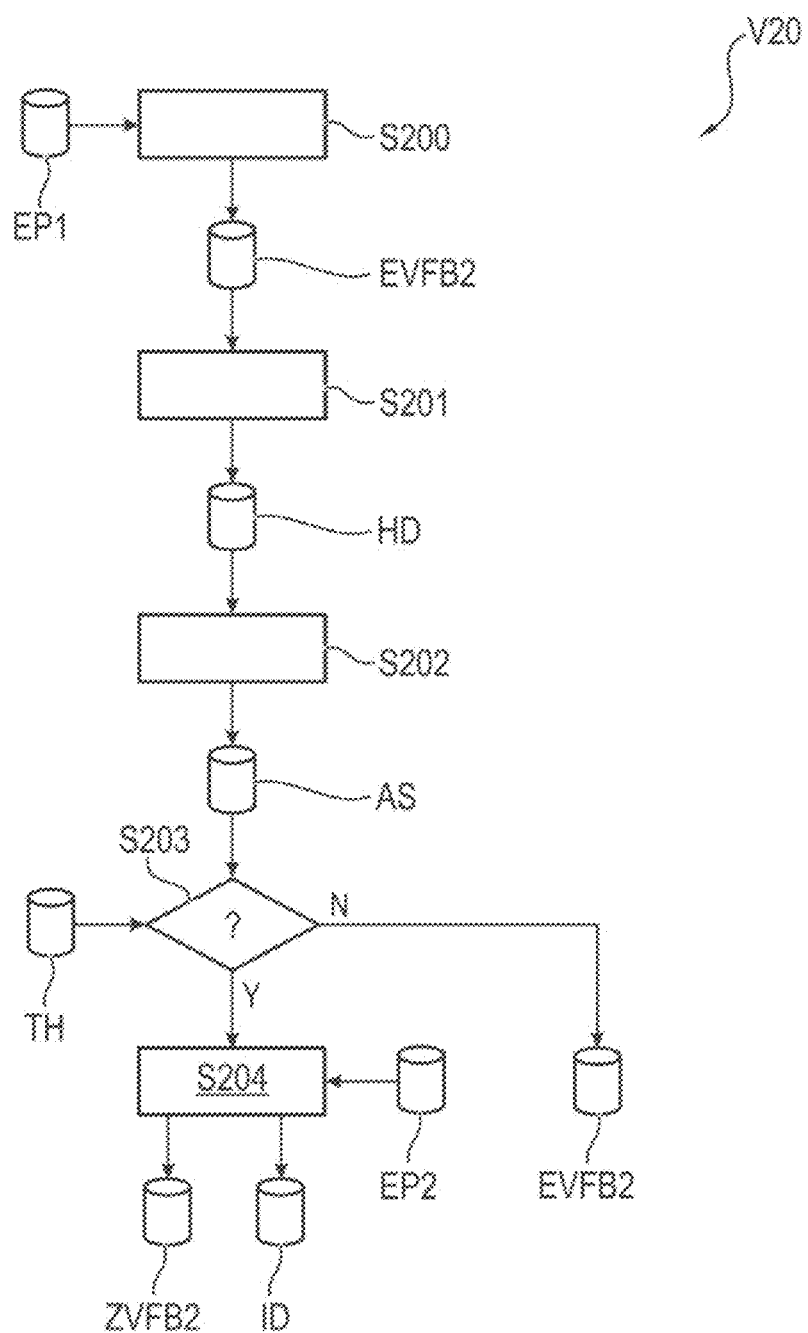
FIG. 31 shows steps of a method for an acquisition of a second fluorescence image according to a preferred embodiment.

FIG. 27 shows pixel values of a subordinate image,

FIG. 28 shows respective confidence measure values for respective second sub-images of a second fluorescence image, FIG. 29 shows steps of a method for an acquisition of a first fluorescence image according to a preferred first embodiment, FIG. 30 shows steps of a method for an acquisition of a first fluorescence image according to a preferred second embodiment, and FIG. 31 shows steps of a method for an acquisition of a second fluorescence image according to a preferred embodiment.

FIG. 13 illustrates different steps for carrying out the method according to the invention. In a step S1, a substrate which has multiple *Crithidia luciliae* cells is provided. In a step S2, the substrate is incubated with the patient sample. The patient sample potentially has the autoantibodies. In a step S3, the substrate is incubated with a first fluorescent dye. In a step S4, the substrate is incubated with secondary antibodies which have each been labelled with a second fluorescent dye. In a step S5, what takes place is an acquisition of a first fluorescence image of the substrate in a first colour channel which corresponds to the first fluorescent dye. In a step S6, what takes place is an acquisition of a second fluorescence image of the substrate in a second channel which corresponds to the second fluorescent dye. In a step S7, what takes place is an identification of respective first sub-images in the first fluorescence image that each have a *Crithidia luciliae* cell. Such an exemplary first sub-image ETB is depicted in FIG. 5. In a subsequent step S8, what takes place is a determination of respective second sub-images of the second fluorescence image that correspond to the respective first sub-images of the first fluorescence image. Such an exemplary second sub-image ZTB is depicted in FIG. 6 and corresponds to the first sub-image ETB from FIG. 5. In a step S9, what takes place is a respective processing of at least one subset of the respective second sub-images by means of a pretrained convolutional neural network for determining respective binding measures which indicate a respective extent of a binding of autoantibodies in a respective kinetoplast region of a respective *Crithidia luciliae* cell of a respective second sub-image. In a step S10, what takes place is a determination of an overall binding measure with regard to the binding of autoantibodies from the patient sample to double-stranded DNA in the substrate on the basis of the respective binding measures of the respective second sub-images. In a step S11, what preferably takes place is a provision of the overall binding measure and what alternatively or additionally takes place is an outputting and/or displaying of the overall binding measure.

FIG. 14a shows an exemplary, in particular partial, processing of a specific second sub-image region ZTB1 by a convolutional neural network for determining a respective, individual binding measure IBM1. The binding measure IBM1 indicates an individual extent of a binding of autoantibodies in an individual kinetoplast region of an individual *Crithidia luciliae* cell of the individual second sub-image region ZTB1.

FIG. 14b illustrates a determination of the overall binding measure GBM by an ascertainment step ERS, which corresponds to the step S10 from FIG. 13, for determining the overall binding measure GBM on the basis of respective binding measures IBM1, IBM2 of respective second sub-images.

FIG. 7 illustrates an exemplary embodiment of the device V1 according to the invention. The device V1 comprises a mounting device H for the substrate S. Excitation light AL from an excitation light source LQ is prefiltered via an optical filter F1 and then guided through an optics unit O by means of a dichroic mirror SP1 towards the substrate. Resultant fluorescence radiation or resultant fluorescence light FL then passes from the substrate back through the objective O through the dichroic mirror SP1 and through a final filter F2. The optical filter F2 filters out a wavelength of the excitation radiation or the excitation light AL. The fluorescence light FL is then supplied to at least one image acquisition unit in the form of a camera K1 and preferably a further camera K2. Via a dichroic mirror SP2, the fluorescence light FL is split. Via an optical filter FR, fluorescence light FL1 of a first colour channel, preferably a red colour channel, is filtered out and supplied to the image acquisition unit K1. The image acquisition unit K1 acquires a first fluorescence image of the substrate S in the first colour channel. Via an optical filter FG, fluorescence radiation FL2 of the second colour channel, preferably the green colour channel, is filtered out and supplied to the image acquisition unit K2, which acquires a second fluorescence image of the substrate S in the second colour channel. Via a data interface DS1, the device V1 can provide result data ED which indicate the overall binding measure.

A computing unit R is designed to receive the first fluorescence image in the form of digital data BI1. Furthermore, the computing unit R is designed to receive the second fluorescence image in the form of digital data BI12. The computing unit R is furthermore designed to carry out the steps S7 to S10 of the method according to the invention.

A computing unit R according to the invention can also be realized as depicted in FIG. 20.

Here, the computing unit R receives the first fluorescence image BI1 and the second fluorescence image BI2 via at least one data interface DS2 in the form of at least one data signal SI. After carrying out the relevant steps S7 to S10 of the method according to the invention from FIG. 13, the computing unit R has determined the overall binding measure of the binding of autoantibodies from the patient sample to double-stranded DNA. Preferably, the computing unit R comprises an output interface AS in relation to a display unit AE, via which the overall binding measure can be output or displayed. Preferably, the computing unit R comprises a further data interface DS3 towards a data network, via which data interface the computing unit provides the overall binding measure via a data signal S13. The data interfaces DS2, DS3 of the computing unit R can also be a common data interface. The data interfaces DS2, DS3 are preferably network data interfaces.

The computing unit R can also be part of a data network device DV according to the invention, as illustrated in FIG. 21. The data network device DV comprises at least one data interface DS4 for receiving the first fluorescence image BI1 and the second fluorescence image BI2 by means of at least one data signal SI1. The data network device DV comprises the computing unit R, which is preferably connected to a storage unit MEM and the data interface DS4 via an internal data bus IDB. The computing unit R is designed in that manner as previously described with regard to FIG. 20. The data network device DV can be an individual computer or else a so-called cloud solution. The data network device DV thus carries out, by means of the computing unit R, a method according to the invention for digital image processing, in which method the fluorescence images BI1, BI2 are received and in which method the computing unit R carries out the steps S7 to S10 from FIG. 13.

FIG. 22 illustrates a computer program product CPP according to the invention, which comprises commands which, upon the execution of the program by a computer CO, prompt said computer to carry out a digital image-processing method according to the invention.

The computer program product CPP can be provided in the form of a data carrier signal S12 and be received by a computer CO by means of a data interface DSX situated on the computer CO. The data carrier signal SI2 thus transmits the computer program product CPP.

FIG. 15 illustrates sub-steps S71, S72, S73 as subordinate steps of the step S7 for identifying first sub-image regions ETB, which are depicted in FIG. 5. The fluorescence image SR from FIG. 3 is modified in terms of its contrast in a sub-step S71 by means of the so-called CLAHE method (contrast limited adaptive histogram equalization), yielding the modified fluorescence image KSR from FIG. 8. By means of OTSU's thresholding method, what is then obtained in the step S72 on the basis of the image KSR from FIG. 8 is a binary image BSR from FIG. 9. Said binary image from FIG. 9 is then post-processed by means of the method "*Satoshi Suzuki and others. Topological structural analysis of digitized binary images by border following. Computer Vision, Graphics, and Image Processing.* 30(1): 32-46, 1985" in order to find relevant contours in the image BSR. Furthermore, in the step S73, so-called bounding boxes are then post-processed by means of the function boundingRect from the section "Structural analysis and shape descriptors" from the database OpenCV (https://opencv.org). Here, the bounding boxes have a size of 150×150 pixels. For the CLAHE method, rectangular regions of size 64×64 pixels can be used. This then gives rise to bounding boxes as first sub-image regions ETB, as depicted in FIG. 5.

Preferably, the fluorescence image SR from FIG. 3 can be assessed in terms of its quality, by at least ten identified cell regions or second sub-images having to have a specific morphology and a certain minimum size after ascertainment of the contours in the image BSR from FIG. 9. Only when at least ten cells meet both these criteria is there then a further processing of the fluorescence images without error output in the method. If fewer than ten identified cell regions or second sub-images fail to meet the two criteria, the method is preferably aborted and an error message output.

FIG. 16a illustrates different processing levels P1, P2, P3, P4 of the convolutional neural network CNN for determining the overall binding measure GBM on the basis of multiple second sub-image regions ZTB1 . . . . ZTBN as explained above. Here, the CNN processes respective second sub-image regions ZTB1, ZTB2, . . . , ZTBN separately in order to then generate a respective individual binding measure IBM1, IBM2, . . . , IBMN for a respective second sub-image region ZTB1, ZTB2, . . . , ZTBN, as explained above with regard to FIG. 14a.

Here, FIG. 16a shows that, in the course of this determination of the respective individual binding measures for each individual second sub-image ZTB1, . . . , what is then generated is a respective final feature map FFM1 and preferably a further final feature map FFM2. The CNN can be configured such that only a single final feature map FFM1 of a single channel is provided and is generated.

The result of the processing level P3 from FIG. 16a is thus the final feature map FFM1 and preferably the final feature map FFM2 for a second sub-image ZTB. The first final feature map FFM1 is depicted in FIG. 10b for the second sub-image ZTB from FIG. 10a. The second final feature map FFM2 for the second sub-image ZTB is depicted in FIG. 10c.

The CNN solves the problem of a so-called "single-label classification", i.e. whether the kinetoplast in the second sub-image has a staining or not. The final feature map FFM1 represents an activation in a first classification channel with regard to a positive decision from the "single-label classification". i.e. that the kinetoplast region is stained. The final feature map FFM2 to be preferably provided represents the corresponding activation with regard to a negative decision, i.e. that the kinetoplast is not significantly stained.

According to FIG. 17, the first final feature map FFM1 and preferably the second final feature map FFM2 are then used as the basis to determine a positive confidence measure PK with regard to a staining of the kinetoplast region or to a presence of a binding of autoantibodies in the corresponding kinetoplast region K of the second sub-image ZTB.

Preferably, the first final feature map FFM1 and preferably the second final feature map FFM2 are used as the basis to determine a negative confidence measure NK with regard to a staining of the kinetoplast region or to a presence of a binding of autoantibodies in the corresponding kinetoplast region K of the second sub-image ZTB.

Preferably, only the first final feature map can be used as the basis to determine a confidence measure based on a presence of a binding of autoantibodies in a respective kinetoplast region for the respective second sub-image ZTB, without having to use the second final feature map FFM2. It is then, for example, possible in a step S20 to supply the feature map FFM1 to a so-called max pooling, which ascertains for the final feature map FFM1 the maximum pixel value as an individual scalar value. Preferably, said scalar value can be used as the confidence measure. Preferably, said scalar value can then, for example, be used as the basis to ascertain by means of a so-called sigmoid function a value as the confidence measure. Preferably, said scalar value can then, for example, be used as the basis to ascertain by means of a so-called rectified linear unit activation function a value as the confidence measure.

Preferably, in respective steps S20, the two respective feature maps FFM1, FFM2 are each supplied to a so-called max pooling, which in each case ascertains for a respective final feature map the maximum pixel value as a respective individual scalar value. On the basis of said scalar values, it is then possible in a so-called Softmax function in a step S21 to determine a positive probability PK as the confidence measure with regard to the presence of the binding of autoantibodies in the kinetoplast region or with regard to a staining of the kinetoplast region. The negative probability NK can likewise be determined by the Softmax function. Positive probability PK and negative probability NK preferably form a sum total of value 1 when added. In this way, for a respective second sub-image ZTB, it is thus possible as a result of ascertainment of the first final feature map FFM1 and preferably also the second final feature map FFM2 to then determine according to FIG. 17 a respective confidence measure with regard to the presence of the binding of autoantibodies in the kinetoplast region of the second sub-image.

Functions which are an alternative to the Softmax function are, for example, the sigmoid function, the rectified linear unit activation function or the leaky rectified linear unit activation function.

FIG. 18 shows steps for a selection of a subset of the second sub-images from the second fluorescence image on the basis of the respective positive confidence measures for the second sub-images. The positive confidence measures PK1, PK2, PK3, . . . , PKN with index 1, . . . . N of N different second sub-images are sorted in ascending order with respect to their value in a step S30. By way of example, for 29 different *Crithidia luciliae* cells or for 29 different second sub-images from a second fluorescence image, FIG. 28 shows the respectively associated positive confidence measures PK, which are plotted in ascending value with regard to their values PKW via a corresponding sorting index 1 . . . . , 29. In the step S31, what are then selected are those confidence measures and their respectively associated second sub-images, the associated confidence measure values of which are 50% of the highest confidence measure values PKW. This subordinate set of the associated second sub-images is then output or indicated by outputting of the corresponding sub-image indices by means of a data set ID. On the basis of the indices from the data set ID, it is then possible to select the corresponding second sub-images and their associated binding measures for a determination of the overall binding measure.

The overall binding measure is then determined on the basis of those binding measures which belong to the selected second sub-images. Such an ascertainment of the overall binding measure takes place especially in a post-processing PP step within the fourth processing level P4 of the convolutional neural network, as depicted in FIG. 16a.

FIG. 19 shows again an exemplary processing of an individual second sub-image ZTB1 by the convolutional neural network CNN. First of all, the second sub-image ZTB1 is processed by the first three processing levels P1 to P3 of the convolutional neural network, with the result that the final feature map FFM1 and preferably also the second final feature map are provided. In a selection step SEL, what then takes place on the basis of the index data ID elucidated with regard to FIGS. 17 and 18 is the potential selection of the second sub-image ZTB1 into the subset of the second sub-images. If the sub-image ZTB1 has been selected into said subset, what then takes place is further processing as post-processing PP in the fourth processing level P4. Here, after determination of the positive confidence measures and after the selection of the subset of second sub-images, what then takes place is a respective post-processing of the respective first feature maps of the selected respective second sub-images. By way of example, what is thus shown here for an individual second sub-image ZTB1 is a post-processing PP for determining an individual binding measure IBM1. Here, what takes place for the second sub-image ZTB1 is a selection of a respective subordinate image on the basis of the final feature map FFM1. The subordinate image presents a respective kinetoplast region of the corresponding *Crithidia luciliae* cell in the second sub-image. Such a second sub-image ZTB is depicted in FIG. 10*a* by way of example. The associated first feature map FFM1 from FIG. 10*b* is then, in a step KIN, adapted in terms of its size and resolution to the second sub-image ZTB from FIG. 10*a* by means of cubic interpolation, resulting in the enlarged feature map VFM from FIG. 11*a*.

In a thresholding step SB, a binary-value mask BM, which is depicted in FIG. 11, is then ascertained. Here, the threshold value preferably used is that value which is half of the maximum possible grey-value intensity of a feature map. Thus, if a grey value of a feature map VFM is between the values 0 and 1, the value 0.5 is used as threshold value.

In a step MS, the masking operator BM from FIG. 11*b* is then applied to the second sub-image ZTB, yielding the corresponding subordinate image SUB from FIG. 11*c*. For each respective second sub-image ZTB, the proposed convolutional neural network CNN is thus capable of providing a final feature map FFM1 which indicates by means of its values a subordinate-image region for the second sub-image that corresponds to the kinetoplast. The convolutional neural network is thus capable of cutting out or selecting a corresponding subordinate image from the second sub-image that can then be used for the determination of a binding measure of a binding of autoantibodies to double-stranded DNA on the kinetoplasts.

According to FIG. 19, what is then determined in a determination step BS is the binding measure IBM1 for the second sub-image ZTB1. This is done by looking at the pixel values from the subordinate image SUB and choosing that value which defines the 90% quantile for the pixel values from the subordinate image. In relation to this, FIG. 27 shows, for the pixels of the subordinate image SUB from FIG. 11*c*, the corresponding pixel values PW in ascending size with corresponding sorting index PN. The value QW for the index QN is that value for which 90% of the pixel values from the subordinate image SUB are smaller than the value QW.

In a following step, the multiple individual binding measures IBM1, IBM2 . . . of the individual second sub-images from the selected subset are then used as the basis to determine the overall binding measure GBM.

Figure 12A:
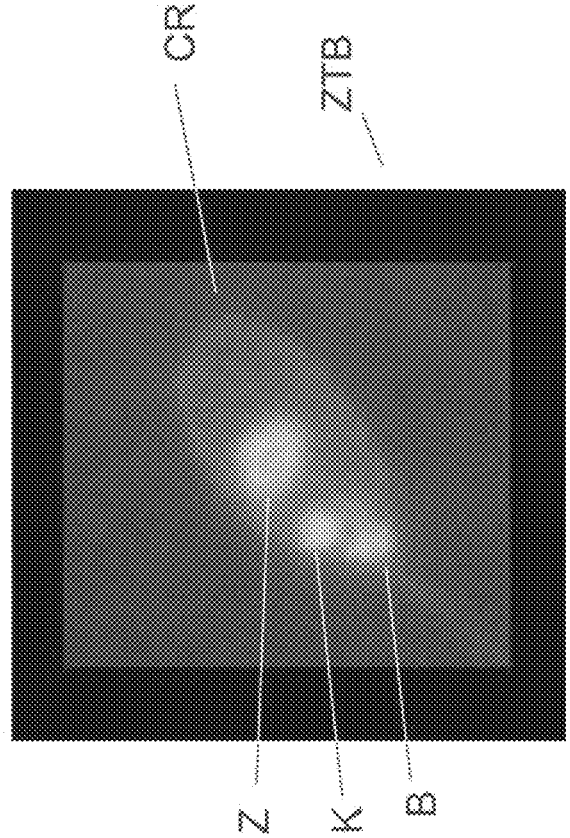
FIG. 12*a* shows again the second sub-image.

For the second sub-image from FIG. 12*a*, FIG. 12*b* shows an indicated region IND which approximately indicates the region of the subordinate image SUB from FIG. 11*c*. It can be clearly seen that the selection of the subordinate-image region by the convolutional neural network was successful here for identifying the kinetoplast.

FIG. 16*a* shows an exemplary embodiment of the convolutional neural network CNN with multiple processing levels P1, P2, P3, P4.

In a first processing level P1, the CNN generates a first set of two-dimensional resultant feature maps RFM1 on the basis of a second sub-image ZTB by means of at least one first convolutional layer LA1 and by means of application of multiple two-dimensional convolution kernels. Said feature maps RFM1 need not come directly out of the convolutional layer LA1, but can be generated by means of further processing steps PS2, PS3, PSC.

In the convolutional layer LA1, what takes place is a processing in a step PS1 with a sequence of different sub-steps. The step PS1 is of the type of a step PSA, which is depicted in detail in FIG. 16*b*. What takes place first of all is a two-dimensional convolution CONV2D of the incoming second sub-image with multiple convolution kernels by means of respective two-dimensional convolutions. A subsequent batch normalization takes place in a step BN. What then follows is a so-called activation in a step ACT.

In the context of this application, a convolutional layer has a layer for convoluting one or more feature maps with one or more convolution kernels. Such a layer for convolution can preferably then be followed within the convolutional layer by a batch normalization layer and/or an activation layer.

In a second processing level P2 from FIG. 16*a*, what then takes place is a generation of a second set of two-dimensional resultant feature maps RFM2 on the basis of the first set of feature maps RFM1 by means of at least one second convolutional layer LA2 and by means of application of multiple three-dimensional convolution kernels.

On the basis of the second set RFM2, what then takes place is a generation of a third set of two-dimensional resultant feature maps RFM3 by means of at least one third convolutional layer LA3 and by means of application of multiple three-dimensional convolution kernels. Said third set RFM3 enters directly or indirectly into the further processing of the third level P3. In the third level, what takes place is a determination of the first final feature map FFM1 and preferably the second final feature map FFM2 on the basis of the third set RFM3 by means of further convolutional layers LAX.

The second set RFM2 has a smaller number of feature maps than the first set RFM1. Furthermore, the third set RFM3 has a larger number of resultant feature maps than the second set RFM2. A convolution kernel can also be referred to as a convolution operator.

The reduction in the number of feature maps in the second convolutional layer LA2 results in a so-called squeezing. The feature maps of the first set RFM1 or the features thereof are projected into a subspace by means of the convolution kernel, since the three-dimensional convolution kernels respond to feature correlation between the feature maps. Thus, only the most dominant features from the feature maps of the first set RFM1 are retained and projected into feature maps of the second set RFM2. Less dominant and less informative features are thus filtered out as a result.

As a result of the increase in the number of feature maps by the third convolutional layer LA3 from the second set RFM2 towards the third set RFM3, the previously reduced features or information items are distributed among different feature spaces and different feature maps, it being possible to combine the features in different ways owing to the degrees of freedom of the three-dimensional convolution kernels used in the third convolutional layer LA3. This corresponds to a so-called expand.

In the first processing level P1, the first convolutional layer LA1 can be followed by a further convolutional layer LA11. Said layer LA11 uses the feature maps created in the layer LA1. Preferably, the layer LA11 has procession steps PS2. PS3 arranged in parallel to one another. Said procession steps PS2, PS3 are, in each case, of the type of the procession step PSB from FIG. 16*c*. In a sub-step CONV3D of the step PSB, what takes place is a three-dimensional convolution of the feature maps with respective three-dimensional convolution kernels. What then follows in a further sub-step BN is a so-called batch normalization. What further follows in a step ACT is a so-called activation.

The feature maps resulting from the steps PS2 and PS3 of the layer LA11 are then concatenated with one another in a concatenation step PSC: in other words, the feature maps are joined together.

Preferably, in the first processing level P1, what takes place furthermore is a convolution of the second sub-image ZTB in a step PS4 with two-dimensional convolution kernels. The step PS4 is of the type sub-step CONV2D from FIG. 16b.

Preferably, the feature maps resulting from the layer LA11 and from the step PS4 can be linked to one another such that the entries of the feature maps are in each case added together in an element-wise manner. Thus, this does not give rise to any change in the dimensionality of the feature maps; instead, the individual elements of the feature maps from the layer LA11 are added in an element-wise manner with the individual elements of the feature maps from the step PS4.

The step PS5 from the second convolutional layer LA2 is of the type step PSB from FIG. 16c.

Preferably, the feature maps from the convolutional layer LA2 are processed in the third convolutional layer LA3 such that, in corresponding steps PS7 and PS8 and in the step PSC, the feature maps are processed in an analogous manner to those from the convolutional layer 11, it being possible for a number of convolution kernels used and a dimensionality of the convolution kernels to deviate from one another. The steps PS7 and PS8 are of the type of the step PSB from FIG. 16c. As a result of an element-wise addition of the respective feature maps from the respective steps PS7 and PS8, what is then generated by a step PSC is a third set of feature maps RFM3.

In the second processing level P2, the second convolutional layer LA2 and the third convolutional layer LA3 are in a sequence as sub-steps of a sequential processing path PF1. Furthermore, in the second processing level P2, there is in parallel to the sequential processing path PF1 a further processing path PF2 in which the CNN generates a fourth set RFM4 of two-dimensional resultant feature maps on the basis of the first set RFM1 by means of at least one fourth convolutional layer LA4 and by means of application of multiple three-dimensional convolution kernels. This is done by a step PS6, which is of the type sub-step CONV3D from FIG. 16c.

A set of feature maps RFM5 that is determined by the step PSS in the processing level P2 is then generated in turn from the third set RFM3 of feature maps and the fourth set RFM4 of feature maps by means of a step PSS. Said set of feature maps RFM5 can then be used in a third processing level P3 in order to generate the first final feature map FFM1 and preferably the second final feature map FFM2 by means of further steps LAX, which will be explained in detail later.

In a further processing level PS4, so-called post-processing then takes place, as explained in detail in FIG. 19.

The CNN thus generates the final feature map FFM1 corresponding to the second sub-image ZTB on the basis of the third set RFM3 of feature maps and on the basis of the fourth set RFM4 of feature maps. Here, the number of successive convolutional layers LA4 in the parallel processing path PF2 is smaller than the number of successive convolutional layers LA2, LA3 in the sequential processing path PF1. The parallel processing path PF2 thus has fewer convolutional layers than the sequential path PF1. What is made possible as a result in the course of a training of the convolutional neural network is that, in the event of a recalculation of individual weights of the convolution kernels in the course of a backpropagation, the problem of the so-called vanishing gradient is avoided or reduced.

As stated above with regard to FIG. 16a, the CNN can consist of four processing levels.

In relation to this, FIG. 23 shows a detailed embodiment of the first processing level P1, which corresponds to the first processing level P1 from FIG. 16a.

For each individual step, the dimensionality of an input variable in the form of a second sub-image or a set of feature maps is specified in detail. In this connection, for each individual step, the dimensionality of the input variable(s) can be found in the top row "Input" between subsequent brackets through the second and third entry. For example, the second sub-image data ZTB1 are of a dimensionality of 150×150 pixels. For the data ZTB1, there is only a single input variable, which is indicated by the element "1" in the fourth/last entry between the brackets. In terms of the value range, the image data ZTB1 are preferably normalized to a value range of from 0 to 1.

In the step PS, said input variable ZTB1 is, for example, then processed with a convolution kernel such that feature maps of a dimensionality of 75×75 pixels result. In this connection, the last entry in the bottom row "Output" indicates the number of generated feature maps in the resultant set of feature maps. As a result, for each processing step, a person skilled in the art can thus clearly deduce from the parameters specified here, how many convolution kernels must be applied to incoming data ZTB1 or incoming feature maps in order to arrive at a specific number of outgoing feature maps. In the example step PS4, these are 64 convolution kernels. Furthermore, a person skilled in the art can deduce on the basis of the specified dimensionality of the incoming feature maps and the specified dimensionality of the outgoing feature maps, how far a so-called striding, i.e. a shift during the convolution of a feature map with a convolution kernel, must be performed by a specific number of pixels. In the example of step PS4, this is a striding of the value 2.

A person skilled in the art is given clear instructions for configuring the processing level P1 of the CNN by the information specified in FIG. 23.

FIG. 24 shows a first part P21 of the processing level P2 from FIG. 16a. Here, the structure of the sub-processing level P21 substantially corresponds to the processing level P2 from FIG. 16a. In addition, there is further provided here a so-called dropout step for the training phase, in which individual entries of the feature maps are set to the value "0" (zero) in terms of their pixel values during the training, but not during the actual classification in the test phase. Here, the drop factor is preferably a value of 50%, meaning that half of the pixel values are set to zero. The pixel values are randomly chosen, by selection of their indices by means of a random function.

What then results in the sub-processing level P21 is the set RFM5 of feature maps, as shown above in the processing level P2 in FIG. 16a.

Preferably, the CNN can have a further sub-processing level P22, which was not depicted above in FIG. 16a. Here, the set of feature maps RFM5 is further processed in order to generate a modified set of feature maps RFM51.

Here too, FIG. 25 contains precise information for a person skilled in the art as to how said modified set of feature maps RFM51 is to be generated. Here too, a so-called dropout DRO takes place during the training phase, but not the test phase.

FIG. 26 shows one embodiment of the third processing level P3 for generating the first final feature map FFM1 and preferably the second final feature map FFM2. The feature map FFM1 and preferably the feature map FFM2 are generated indirectly on the basis of the third set of feature maps RFM3 and the fourth set RFM4 of feature maps. Here, the processing step LAX, which was depicted above in FIG. 16a, has sub-steps. In a first sub-step SEPC, what takes place is a so-called "depth-wise convolution" of the incoming feature maps RFM51, in which each individual two-dimensional feature map from the set RFM51 is separately convoluted with a two-dimensional convolution kernel, yielding a set of two-dimensional feature maps RFM511. What then takes place immediately afterwards in a further sub-step CONV3D is a convolution of the multiple two-dimensional feature maps of the set RFM511 that result from the step SEPC with a three-dimensional convolution kernel of the dimensionality 1×1×G, where G is the number of feature maps in the set, with the result that the first final feature map FFM1 is determined therefrom. Preferably, what also takes place furthermore in the further sub-step CONV3D is a further convolution of the multiple two-dimensional feature maps of the set RFM511 that result from the step SEPC with a further three-dimensional convolution kernel of the dimensionality 1×1×G, where G is the number of feature maps in the set, with the result that the second final feature map FFM2 is determined therefrom.

The third processing level P3 from FIG. 26 is then followed by so-called post-processing PP, as indicated in the processing level P4 in FIG. 16a and as explained in detail in FIG. 19.

For an implementation of one or more exemplary embodiments of the convolutional neural network proposed here, a person skilled in the art can have recourse to a so-called open-source deep-learning library called "Keras". Detailed information is found under https://keras.io by a person skilled in the art. The embodiment of the proposed CNN with the processing levels P1, P21, P22 and P3 from FIGS. 23 to 26 and also the processing level P4, as illustrated in detail in FIG. 19, was created for test purposes by means of the so-called open-source deep-learning library "Keras". Two data sets of fluorescence images were used.

The first data set of fluorescence images was one in which it was known that the patient samples used for incubation have autoantibodies and that the kinetoplast regions thus have a relevant staining in the fluorescence images. The second data set of fluorescence images was one in which it was known that the patient samples used for incubation have no antibodies and that the kinetoplast regions thus have no relevant staining in the fluorescence images.

By means of a pre-processing of the first data set of fluorescence images in the manner described in detail here, what was then determined from the corresponding first fluorescence images was altogether approx. 23,000 first sub-images and thus also approx. 23,000 corresponding second sub-images of the second fluorescence images, for which there was precisely a binding of autoantibodies from a patient sample to dsDNA in the kinetoplast region, meaning that the kinetoplast region had a significant staining and therefore a positive classification decision has to be made.

By means of a pre-processing of the second data set of fluorescence images in the manner described in detail here, what was then determined from the corresponding first fluorescence images was altogether approx. 23,000 first sub-images and thus also approx. 23,000 corresponding second sub-images of the second fluorescence images, for which there was precisely no binding of autoantibodies from a patient sample to dsDNA in the kinetoplast region, meaning that the kinetoplast region had no significant staining and therefore a negative classification decision has to be made.

From the approx. 23,000 second sub-images to be rated as positive, approx. 18,000 second sub-images were used for a training phase of the CNN. The further approx. 5,000 positive second sub-images were used for a test phase. From the 23,000 second sub-images to be rated as negative, approx. 18,000 were used for a training phase of the CNN. The further approx. 5,000 negative second sub-images were used for a test phase.

The CNN was trained in 100 epochs using a learning rate of 1e-3.

With regard to a decision as to whether a second sub-image from the 10,000 second sub-images was correctly rated as positive or negative in the test phase by means of the CNN on the basis of the confidence measures PK and NK, the result was a sensitivity of 95.7% and a specificity of 98.1%.

FIG. 29 shows method steps V10, by means of which the first fluorescence image of the first colour channel is determined by means of at least one first preliminary fluorescence image.

Using a predefined acquisition parameter GF, which is preferably a gain parameter for a scaling of acquired grey values, a first preliminary fluorescence image EVFB1 is acquired in the first colour channel. In a step S101, a histogram is then created across the pixel values of the first preliminary fluorescence image EVFB1. By means of the histogram, a threshold value is then determined as a grey value, which is applied to the pixel values of the first preliminary fluorescence image EVFB1. Here, it is, for example, possible to first determine the peak value of the histogram and to then determine the grey value belonging to the peak value. Said grey value can then preferably be increased by a predefined value of five pixel values in order to thus determine the threshold value. Pixel values of the image EVFB1 that are below said threshold value are then classified as background and do not go into a modified first preliminary fluorescence image EVFB1'. The modified first preliminary fluorescence image EVFB1' then represents those pixel values which exceed the predetermined threshold value.

On the basis of these pixel values of the image EVFB1', the mean is then formed across said pixel values in the step S102 in order to determine a brightness value HW.

In a step S103, the acquisition parameter GF is then modified depending on the brightness value HW in order to determine a modified acquisition parameter GF2. What is preferably done here is division of a predefined parameter value, for example a target grey value of the value 55 for a quantization range of from 0 to 255, by the brightness value HW and then multiplication thereof by the previously predefined acquisition parameter GF, as per GF2=(55/HW)× GF. This thus achieves a scaling of the predefined acquisition parameter GF by the brightness value HW in order to determine a modified acquisition parameter GF2. This acquisition parameter is preferably simply a modified gain parameter GF2.

Using the modified acquisition parameter GF2, a second preliminary fluorescence image ZVFB1 is then acquired in a step S104 and is then used as the first fluorescence image of the first colour channel SR: see FIG. 3.

FIG. 30 shows one variant V11 of the method V10 from FIG. 29. The method V11 from FIG. 30 comprises an additional step S110, in which a check is made as to whether the brightness value of the first preliminary fluorescence image EVFB1 corresponds to an expected brightness value EHW. For example, for an exemplary quantization range of from 0 to 255 of the grey values, the brightness value HW can then correspond to an expected brightness value EHW if it falls within an interval of from 45 to 60. In this case, there is then branching from the step S110 towards an output of the first preliminary fluorescence image EVFB1, with the result that said image EVFB1 is used as the first fluorescence image SR of the first colour channel; see FIG. 3.

If the brightness value HW does not correspond to the expected brightness value, a modified acquisition parameter GF2 is determined in a step S103 depending on the previously determined brightness value HW. Preferably, in the event that the brightness value HW falls within a value range of from 30 to 45, the modified acquisition parameter GF2 can be determined as the acquisition parameter GF scaled by a factor of 1.75, as per GF2=1.75×GF. Preferably, in the event that the brightness value HW falls within a value range of from 60 to 70, the modified acquisition parameter GF2 can be determined as the acquisition parameter GF scaled by factor of 0.625, as per GF2=0.625×GF.

Relevant boundary values of value ranges and relevant scaling factors can be provided as default data VD.

In the step S104, a second preliminary fluorescence image ZVFB1 is then acquired using the modified acquisition parameter GF2. The second preliminary fluorescence image ZVFB1 is then used as the first fluorescence image SR of the first colour channel; see FIG. 3.

FIG. 31 shows a method V20, in which preferably performable steps for acquiring the second fluorescence image of the second colour channel are carried out.

In a step S200, a first preliminary fluorescence image EVFB2 is acquired in the second colour channel by means of at least one predefined acquisition parameter EP1, which is preferably a gain parameter.

In a step S201, a histogram is then formed across the pixel values of the image EVFB2, with the result that the histogram data HD are ascertained and provided.

In a step S202, the number of pixels exceeding a specific saturation with respect to a brightness is then established. For an exemplary quantization range of the pixel values of from 0 to 255, what is established for example is how many pixels have a pixel value or a grey value of 255. This number of pixels which are in brightness saturation are provided as data AS.

In a step S203, a check is then made as to whether the number of pixels AS which are within a saturation range exceeds a predefined threshold value TH. If there is no exceeding of the threshold value (see branch "N"), the first preliminary fluorescence image of the second colour channel EVFB2 is used as the second fluorescence image of the second colour channel SG: see FIG. 4. If the number of pixels which are in saturation exceed the threshold value TH (see branch "Y"), a second preliminary fluorescence image ZVFB2 is acquired in the second colour channel in a step S204 using at least one second predefined acquisition parameter EP2. The predefined acquisition parameter EP2 differs from the previously predefined first acquisition parameter EP1. Preferably, the acquisition parameter EP2 is a gain parameter and is smaller than the first acquisition parameter EP1, meaning that the image ZVFB2 is lit less strongly than the image EVFB2. The acquired second preliminary fluorescence image EVFB2 is then used as the second fluorescence image SG of the second colour channel: see FIG. 4. Preferably, what are furthermore provided are indicator data which indicate that the brightness of the first preliminary fluorescence image EVFB2 has exceeded a maximum brightness and that the second fluorescence image SG is a second preliminary fluorescence image ZVFB2 of the second colour channel that has been acquired with reduced brightness.

The second preliminary fluorescence image EVFB2 of the second colour channel can then be used in the usual way in the proposed method as the second fluorescence image SG of the second colour channel. Here, the CNN preferably ascertains, by means of a confidence measure PK, whether a staining of kinetoplast regions is present for a minimum number of second sub-image regions, preferably at least ten second sub-image regions. If this is the case, the CNN outputs the maximum brightness or the maximum brightness value, preferably 255, as the overall binding measure. If the CNN establishes that the kinetoplast regions are not really stained, the second fluorescence image SG of the second colour channel is rated as overall negative.

Although some aspects have been described in connection with a device, it is self-evident that these aspects are also a description of the corresponding methods, and so a block or a component of a device is also to be understood as a corresponding method step or as a feature of a method step. Analogously, aspects which have been described in connection with a method step or as a method step are also a description of a corresponding block or detail or feature of a corresponding device.

Depending on specific implementation requirements, it is possible for exemplary embodiments of the invention to realize the computing unit R or the data network device in hardware and/or in software. A computing unit R mentioned here can be realized here as at least one computing unit or else by means of multiple computing units which are associated. Implementation can be effected using a digital storage medium, for example a floppy disc, a DVD, a Blu-Ray disc, a CD, a ROM, a PROM, an EPROM, an EEPROM or a FLASH memory, a hard drive or some other magnetic or optical storage device, which stores electronically readable control signals which interact or can interact with a programmable hardware component such that the respective method is carried out.

As computing unit, a programmable hardware component can be formed by a processor, a central processing unit (CPU), a computer, a computer system, an application-specific integrated circuit (ASIC), an integrated circuit (IC), a system on chip (SOC), a programmable logic element or a field programmable gate array with a microprocessor (FPGA).

The digital storage medium can therefore be machine-readable or computer-readable. Some exemplary embodiments thus encompass a data carrier having electronically readable control signals capable of interacting with a programmable computer system or a programmable hardware component such that one of the methods described here is carried out.

In general, exemplary embodiments or parts of the exemplary embodiments of the present invention can be implemented as a program, firmware, computer program or computer program product with a program code or as data, wherein the program code or the data is/are operative to the effect of carrying out one of the methods or a part of a method when the program runs on a processor or a programmable hardware component.

The invention claimed is:

1. A method for detecting a binding of an autoantibody from a patient sample to double-stranded deoxyribonucleic acid using *Crithidia luciliae* cells by fluorescence microscopy and digital image processing, the method comprising:

incubating a substrate (S) with a patient sample which potentially has the autoantibody, wherein the substrate has multiple *Crithidia luciliae* cells, incubating the substrate (S) with a first fluorescent dye, incubating the substrate (S) with a secondary antibody which has been labelled with a second fluorescent dye, acquiring a first fluorescence image (SR) of the substrate (S) in a first colour channel which corresponds to the first fluorescent dye, acquiring a second fluorescence image (SG) of the substrate (S) in a second colour channel which corresponds to the second fluorescent dye, identifying first sub-images (ETB) in the first fluorescence image (SR) that each represents a *Crithidia luciliae* cell (CR), determining second sub-images (ZTB) of the second fluorescence image (SG) that correspond to the first sub-images (ETB) of the first fluorescence image (SR), for a respective second sub-image (ZTP), selecting a subordinate image (SUB) of the second sub-images (ZTB), the subordinate image (SUB) representing the kinetoplast region (K) of the *Crithidia luciliae* cell (CR), processing at least one subset of the second sub-images (ZTB) by a pretrained convolutional neural network (CNN) for determining binding measures (IBM1, IBM2) which indicate an extent of a binding of the autoantibody in a kinetoplast region (K) of the *Crithidia luciliae* cell (CR) of the second sub-images (ZTB), and determining an overall binding measure (GBM) with regard to the binding of the autoantibody from the patient sample to double-stranded deoxyribonucleic acid on the basis of the binding measures (IBM1, IBM2).

2. The method according to claim 1, further comprising:
for the respective second sub-image (ZTB),
determining the binding measure (IBM1) on the basis of the subordinate image (SUB), and
determining the overall binding measure (GBM) on the basis of the binding measures (IBM1, IBM2).

3. The method according to claim 1, further comprising
determining a final feature map (FFM1) for the second sub-images (ZTB) by the pretrained convolutional neural network (CNN),
determining a confidence measure (PKN) with regard to the presence of the binding of the autoantibody in the kinetoplast region (K) for the second sub-images (ZTB),
selecting the at least one subset of the second sub-images (ZTB) on the basis of the confidence measures (PKN),
processing the final feature maps of the at least one subset of the second sub-images for determining the binding measures (IBM1, IBM2), and
determining the overall binding measure (GBM) on the basis of the binding measures (IBM1, IBM2) of the at least one subset of the second sub-images.

4. The method according to claim 3, further comprising:
for the second sub-images (ZTB) from the selected subset,
selecting the subordinate image (SUB) of the second sub-images (ZTB) on the basis of the final feature map (FFM1) corresponding to the second sub-images (ZTB), the subordinate image (SUB) representing the kinetoplast region (K) of the *Crithidia luciliae* cell (CR), determining the binding measure (IBM1) on the basis of the subordinate image (SUB), and
determining the overall binding measure (GBM) on the basis of the binding measures (IBM1, IBM2).

5. The method according to claim 4, further comprising:
for the second sub-images (ZTB) from the selected subset,
ascertaining a masking operator (BM) on the basis of the final feature map (FFM1),
selecting the subordinate image (SUB) of the second sub-images (ZTB) by applying the masking operator (BM) to the second sub-images (ZTB),
determining the binding measure (IBM1) on the basis of the subordinate image (SUB), and
determining the overall binding measure (GBM) on the basis of the binding measures (IBM1, IBM2).

6. The method according to claim 3, wherein, in the course of a processing of the second sub-images (ZTB), the pretrained convolutional neural network (CNN),
in a first processing level (P1),
generate a first set of resultant feature maps (RFM1) on the basis of the second sub-images (ZTB) by at least one first convolutional layer (LA1) and by applying multiple two-dimensional convolution kernels, and
in a second processing level (P2),
generate a second set of resultant feature maps (RFM2) on the basis of the first set of two-dimensional feature maps (RFM1) by at least one second convolutional layer (LA2) and by applying multiple three-dimensional convolution kernels, and
generate a third set of resultant feature maps (RFM3) on the basis of the second set of two-dimensional feature maps (RFM2) by at least one third convolutional layer (LA3) and by applying the multiple three-dimensional convolution kernels,
wherein the second set (RFM2) has a smaller number of resultant feature maps than the first set (RFM1) and wherein the third set (RFM3) has a larger number of resultant feature maps than the second set (RFM2).

7. The method according to claim 6,
wherein, in the second processing level (P2), the at least one second convolutional layer (LA2) and the at least one third convolutional layer (LA3) are in a sequence as sub-steps of a sequential processing path (PF1),
wherein, in the second processing level (P2), there is in parallel to the sequential processing path (PF1) a further processing path (PF2) in which the convolutional neural network (CNN) generates a fourth set (RFM4) of resultant feature maps on the basis of the first set (RFM1) of two-dimensional feature maps by at least one fourth convolutional layer (LA4),
wherein the convolutional neural network (CNN) generates, on the basis of the third set (RFM3) and the fourth set (RFM4) of resultant feature maps, the final feature map (FFM1) corresponding to the second sub-images (ZTB), and
wherein a number of successive convolution layers in the parallel processing path (PF2) is smaller than a number of successive convolution layers in the sequential processing path (PF1).

8. The method according to claim 1, further comprising:
acquiring a first preliminary fluorescence image (EVB1) in the first colour channel using a predefined acquisition parameter (GF),
determining a brightness value (HW) indicating a brightness of the first preliminary fluorescence image of the first colour channel (EVFB1), modifying the predefined acquisition parameter depending on the brightness value (HW), thus obtaining a modified acquisition parameter,
acquiring a second preliminary fluorescence image (ZVFB1) in the first colour channel using the modified acquisition parameter (GF2),
using the second preliminary fluorescence image of the first colour channel (ZVFB1) as the first fluorescence image (SR) of the first colour channel.

9. The method according to claim 8, further comprising:
acquiring the first preliminary fluorescence image (EVB1) in the first colour channel using the predefined acquisition parameter (GF),
determining the brightness value (HW), indicating the brightness of the first preliminary fluorescence image of the first colour channel (EVFB1), and
establishing, by the brightness value (HW), as to whether the brightness of the first preliminary fluorescence image of the first colour channel (EVFB1) corresponds to an expected brightness,
wherein, in the event of the brightness of the first preliminary fluorescence image (EVFB1) of the first colour channel corresponding to the expected brightness,
using the first preliminary fluorescence image of the first colour channel (EVFB1) as the first fluorescence image (SR) of the first colour channel,
or
wherein, in the event of the brightness of the first preliminary fluorescence image of the first colour channel (EVFB1) not corresponding to the expected brightness,
modifying the predefined acquisition parameter depending on the brightness value (HW), thus obtaining the modified acquisition parameter,
acquiring the second preliminary fluorescence image in the first colour channel (ZVFB1) using the modified acquisition parameter (GF2), and
using the second preliminary fluorescence image of the first colour channel (ZFB1) as the first fluorescence image (SR) of the first colour channel.

10. The method according to claim 1, further comprising:
acquiring a first preliminary fluorescence image (EVFB2) in the second colour channel using a predefined acquisition parameter (EP1), and
establishing whether a brightness of the first preliminary fluorescence image (EVFB2) of the second colour channel exceeds a maximum brightness,
wherein, in the event of the first preliminary fluorescence image of the second colour channel (EVFB2) not exceeding the maximum brightness,
using the first preliminary fluorescence image (EVFB2) as the second fluorescence image (SG) of the second colour channel,
wherein, in the event of the first preliminary fluorescence image of the second colour channel (EVFB2) exceeding the maximum brightness,
acquiring a second preliminary fluorescence image in the second colour channel, (ZVFB2) and
using the second preliminary fluorescence image of the second colour channel (ZVFB2) as the second fluorescence image of the second colour channel (SG).

11. A device (V1) for detecting a binding of an autoantibody from a patient sample to double-stranded deoxyribonucleic acid using *Crithidia luciliae* cells by fluorescence microscopy and digital image processing, comprising:
a mounting device (H) for a substrate (S) which has multiple *Crithidia luciliae* cells (CR) and which has been incubated with a patient sample having an autoantibody, a first fluorescent dye, and a secondary antibody which has been labelled with a second fluorescent dye,
at least one image acquisition unit (K1, K2) for acquiring a first fluorescence image (SR) of the substrate in a first colour channel and a second fluorescence image (SG) of the substrate (S) in a second colour channel, and
at least one non-transitory computer readable medium having stored thereon a plurality of programming instructions that are executable by one or more processors to:
identify first sub-images (ETB) in the first fluorescence image (SR) that each represents at least one *Crithidia luciliae* cell (CR),
determine second sub-images (ZTB) of the second fluorescence image (SG) that correspond to the first sub-images (ETB) of the first fluorescence image (SR),
for a respective second sub-image (ZTP), select a subordinate image (SUB) of the second sub-images (ZTB), the subordinate image (SUB) representing the kinetoplast region (K) of the *Crithidia luciliae* cell (CR),
process at least one subset of the second sub-images (ZTB) by a pretrained convolutional neural network (CNN) for determining binding measures (IBM1, IBM2) which indicate an extent of a binding of the autoantibody in a kinetoplast region (K) of the at least one *Crithidia luciliae* cell (CR) of the second sub-images (ZTB), and
determine an overall binding measure (GBM) of the binding of the autoantibody from the patient sample to double-stranded deoxyribonucleic acid on the basis of the binding measures (IBM1, IBM2).

12. A non-transitory computer readable medium having stored thereon a plurality of programming instructions that are executable by one or more processors to:
receive a first fluorescence image (SR) which represents a staining of a substrate, which in turn has multiple *Crithidia luciliae* cells (CR), by a first fluorescent dye and to receive a second fluorescence image (SG) which represents a staining of the substrate by a second fluorescent dye,
identify first sub-images (ETB) in the first fluorescence image (SR) that each represents at least one *Crithidia luciliae* cell (CR),
determine second sub-images (ZTB) of the second fluorescence image (SG) that correspond to the first sub-images (ETB) of the first fluorescence image (SR),
for a respective second sub-image (ZTP) select a subordinate image (SUB) of the second sub-images (ZTB), the subordinate image (SUB) representing the kinetoplast region (K) of the *Crithidia luciliae* cell (CR),
process at least one subset of the second sub-images (ZTB) by a pretrained convolutional neural network (CNN) for determining binding measures (IBM1, IBM2) which indicate an extent of a binding of an autoantibody in a kinetoplast region (K) of the at least one *Crithidia luciliae* cell (CR) of the second sub-images (ZTB), and
determine an overall binding measure (GBM) of the binding of the autoantibody from a patient sample to double-stranded deoxyribonucleic acid on the basis of the binding measures (IBM1, IBM2).

13. A data network device (DV) comprising:
at least one data interface (DS4) for receiving a first fluorescence image (BI1, SR) which represents a staining of a substrate, which in turn has multiple *Crithidia*

*luciliae* cells, by a first fluorescent dye, and a second fluorescence image (BI2, SG) which represents a staining of the substrate by a second fluorescent dye, and at least one non-transitory computer readable medium having stored thereon a plurality of programming instructions that are executable by one or more processors to, in the course of a digital image processing:

identify first sub-images (ETB) in the first fluorescence image (SR) that each has at least one *Crithidia luciliae* cell (CR), determine second sub-images (ZTB) of the second fluorescence image (SG) that correspond to the first sub-images (ETB) of the first fluorescence image (SR), for a respective second sub-image (ZTP), select a subordinate image (SUB) of the second sub-images (ZTB), the subordinate image (SUB) representing the kinetoplast region (K) of the *Crithidia luciliae* cell (CR), process at least one subset of the second sub-images (ZTB) by a pretrained convolutional neural network (CNN) for determining binding measures (IBM1, IBM2) which indicate an extent of a binding of an autoantibody in a kinetoplast region (K) of the at least one *Crithidia luciliae* cell (CR) of the second sub-images (ZTB), and determine an overall binding measure (GBM) of the binding of the autoantibody from a patient sample to double-stranded deoxyribonucleic acid on the basis of the binding measures (IBM1, IBM2).

14. A method for digital image processing, comprising:

receiving a first fluorescence image (SR), which represents a staining of a substrate (S), which in turn has multiple *Crithidia luciliae* cells (CR), by a first fluorescent dye, and a second fluorescence image (SG) which represents a staining of the substrate (S) by a second fluorescent dye, identifying first sub-images (ETB) in the first fluorescence image (SR) that each represents a *Crithidia luciliae* cell (CR), determining second sub-images (ZTB) of the second fluorescence image (SG) that correspond to the first sub-images (ETB) of the first fluorescence image (SR), for a respective second sub-image (ZTP), selecting a subordinate image (SUB) of the second sub-images (ZTB), the subordinate image (SUB) representing the kinetoplast region (K) of the *Crithidia luciliae* cell (CR), processing at least one subset of the second sub-images (ZTB) by a pretrained convolutional neural network (CNN) for determining binding measures (IBM1, IBM2) which indicate an extent of a binding of an autoantibody in a kinetoplast region (K) of the *Crithidia luciliae* cell (CR) of the second sub-images (ZTB), and determining an overall binding measure (GBM) of the binding of the autoantibody from a patient sample to double-stranded deoxyribonucleic acid on the basis of the binding measures (IBM1, IBM2).

15. A non-transitory computer readable medium having stored thereon a plurality of programming instructions that are executable by one or more processors to carry out the method for digital image processing according to claim 14.

* * * * *